US005763208A

United States Patent [19]
Bischofberger et al.

[11] Patent Number: 5,763,208
[45] Date of Patent: *Jun. 9, 1998

[54] OLIGONUCLEOTIDES AND THEIR ANALOGS CAPABLE OF PASSIVE CELL MEMBRANE PERMEATION

[75] Inventors: Norbert Bischofberger, San Carlos; Ken Kent, Mountain View; Rick Wagner, Burlingame; Chris Buhr, Daly City; Kuei-Ying Lin, Fremont, all of Calif.

[73] Assignee: Gilead Sciences, Inc., Foster City, Calif.

[*] Notice: The term of this patent shall not extend beyond the expiration date of Pat. No. 5,633,360.

[21] Appl. No.: 608,420

[22] Filed: Feb. 28, 1996

Related U.S. Application Data

[63] Continuation of Ser. No. 868,487, Apr. 14, 1992, Pat. No. 5,633,360.
[51] Int. Cl.$^6$ .................. C07H 21/02; C07H 21/04; A61K 31/70
[52] U.S. Cl. .................. 435/40.5; 536/22.1; 536/24.5; 536/24.3; 536/24.31
[58] Field of Search .................. 536/24.5, 24.3, 536/241.31, 22.1; 435/40.5

[56] References Cited

U.S. PATENT DOCUMENTS

| | | |
|---|---|---|
| 4,904,582 | 2/1990 | Tullis . |
| 4,958,013 | 9/1990 | Letsinger . |
| 5,013,830 | 5/1991 | Ohtsuka et al. ............... 536/27 |
| 5,264,423 | 11/1993 | Cohen et al. . |
| 5,420,330 | 5/1995 | Brush ............... 558/185 |
| 5,633,360 | 5/1997 | Bischofberger et al. ............... 536/22.1 |

FOREIGN PATENT DOCUMENTS

| | | |
|---|---|---|
| 1311201 | 12/1992 | Canada . |
| 0 269 574 | 6/1988 | European Pat. Off. . |
| 0 286 028 A2 | 10/1988 | European Pat. Off. . |
| 0.092.574 B1 | 4/1992 | European Pat. Off. . |
| 0 462 145 B1 | 4/1994 | European Pat. Off. . |
| WO 89/12060 | 12/1989 | WIPO . |
| WO 90/10448 | 9/1990 | WIPO . |

OTHER PUBLICATIONS

Clivio et al., "Synthesis of Dinucleoside Phosphates Containing Sulfur Substituted Nucleobases: 4–Thiouracil, 4–Thiothymine and 6–Mercaptopurine," Tet Lett 33:69–72 (1992).
Hobbs et al., "Polynucleotides Containing 2'–Amino–2'–deoxyribose and 2'–Azido–2'deoxyribose," Biochem 12:5138–5145 (1973).
Kumar et al., "Synthesis and Antiviral Activity of Novel 5–(1–Azido–2–haloethyl) and 5–(1–Azido–, amino–, or methoxyethyl) Analogs of 2'–Deoxyuridine," J Med Chem 36:2470–2474 (1993).
Lesnik et al., "Oligodeoxynucleotides Containing 2'–0–Modified Adenosine: Synthesis and Effects on Stability of DNA:RNA Duplexes," Biochem 32:7832–7838 (1993).

Mamos et al., "Straightforward C–8 alkylation of adenosine analogues with tetraalkltin reagents," Tet Lett p. 2413–2416 (1992).
Noonan et al., "Interaction of GTP Derivatives with Cellular and Oncogenic ras–p21 Proteins," J Med Chem 34:1302–1307 (1991).
Pudlo et al., "Synthesis, Antiproliferative, and Antiviral Activity of Certain 4–Substituted and 4,5–Disubstituted 7–[(1,3–Dihydroxy–2–propoxy)methyl]pyrrolo[2,3–d]pyrimidines," J Med Chem 33:1984–1992 (1990).
Ramasamy et al., "A Facile Synthesis of Tubercidin and Related 7–Deazapurine Nucleosides Via The Stereospecific Sodium Salt Glycosylation Procedure," Tet Lett 28(43):5107–5110 (1987).
Robins et al., "Nucleic Acid Related Compounds. 31. Smooth and Efficient Palladium–Copper Catalyzed Coupling of Terminal Alkynes with 5–Iodouracil Nucleosides," Tet Lett 22:421–424 (1981).
Seela et al., "Aminomethylierung von 3,7–Dihydropyrrolo [2,3–d]pyrimidinen an C–5—ein Weg zur Synthese von Aglycon–Analoga des Nucleosids,,Q", CHEM BER III pp. 2925–2930 (1978).
Seela et al., "Mannich–Reaktion am 2–Amino3,7–dihydro-pyrrolo[2,3–d]–pyrimidin–4–on, dem Chromophor des Ribonucleosids,,Q", Chem Ber 110:1462–1469 (1977).
Seela et al., "Synthese von Acyclo–7–desazaguanosin durch regiospezifische Phasentransferalkylierung von 2–Amino–4–methoxy–7H–pyrrolo[2,3–d]pyrimidin," Lebigs Ann. Chem pp. 137–146 (1993).
Seela et al., "Synthesis and Application of Isosteric Purine 2'–Deoxyribofuranosides," Nucls & Nuclt 6(1&2):11–23 (1987).
Sugawara et al., "Studies on the Chemical Synthesis of Potential Antimetabolites. 32. Synthesis of Beta–D–Pentofuranosyldeazaadenines as Candidate Inhibitors for S–Adenosylhomocysteinases and Methyltransferases," Nucls & Nuclt 1(3):239–251 (1982).
Townsend et al., "The Synthesis of 2–Amino–7–(beta–D–ribofuranosyl)pyrrolo[2,3–d]–pyrimidin–4–one (7–Deazaguanosine), a Nucleoside Q and Q* Analog," J HET CHEM 13:1363–1364 (1976).
Winkeler et al., "Synthesis of 2–Amino–7–(2'deoxy–beta–D–erythro–pentofuranosyl)–3,7–dihydro–4H–pyrrolo[2,3–d]pyrimidin–4–one, a New Isotere of 2'–Deoxyguanosine," J Org Chem 48:3119–3122 (1983).

(List continued on next page.)

*Primary Examiner*—Gary L. Kunz
*Attorney, Agent, or Firm*—Daryl D. Muenchau

[57] ABSTRACT

Oligonucleotides that are capable of passive diffusion across cell membranes are disclosed. These oligonucleotides contain at least two nucleotide residues and show a log distribution coefficient in octanol:water of about 0.0–2.5 and a solubility in water of at least 0.001 µg/mL. In preferred embodiments, either at least 80% of the internucleotide linkages are non-ionic, or at least 80% of the bases contain lipophilic hydrocarbyl substitutions, or a combination of these sums to 80%. These oligonucleotides may be conjugated to label and used to visualize cells.

40 Claims, 4 Drawing Sheets

OTHER PUBLICATIONS

Wright et al., "Deoxyribonucleotide Analogs as Inhibitors and Substrates of DNA Polymerase," Pharmaceutical Technology 47:447–497 (1990).

Divakar et al., "Reaction Between 2,2'-Anhydro-1-beta-o-arabinofuranosyluracil and Thiolate Ions," J Chem Soc Perkin Trans I pp. 1625–1628 (1982).

Rottman et al., "Influence of 2'-O-Alkylation on the Structure of Single–Stranded Polynucleotides and the Stability of 2'O-Alkylated Polynucleotide Complexes," BIOCHEM 13(13):2762–2771 (1974).

Agrawal et al., "Oligodeoxynucleoside phosphoramidates and phosphorothioates as inhibitors of human immunodeficiency virus," PROC NATL ACAD SCI 85:7079–7083 (1988).

Akhtar et al., "Interactions of antisense DNA oligonucleotide analogs with phospholipid membranes (liposomes)," NUC ACIDS RES 19:5551–5559 (1991).

Blencowe et al., "Antisense Probin of the Human U4/U6 snRNP with Biotinylated 2'-OMe RNA Oligonucleotides," Cell 59:531–539 (1989).

Chavis et al. "Synthesis of 2',3'-Differentiated Ribonucleosides via Glycosylation Reactions with 2-O-Me or 2-O-TBDMS Ribofuranose Derivatives. 1. Pyrimidine Series," J Org Chem 47:202–206 (1982).

Clare, Susan E., "Deoxyoligoribonucleotides Containing A Single, Site–Specific 2,2,2-Trichloro-1,1-Dimethylethyl Phosphotriester Bond," [Dissertation] (1988).

Codington et al., "Synthesis of 2'-Fluorothymidine, 2'-Fluorodeoxyuridine, and Other 2'-Halogeno-2'-Deoxy Nucleosides," J Org Chem 29:558–564 (1964).

Cotten et al., "2'-O-methyl, 2'-O-ehtyl oligoribonucleotides and phosphorothioate oligodeoxynucleotides as inhibitors of the in vitro U7 snRNP-dependent mRNA processing event," Nuc Acids Res 19:2629–2635 (1991).

Dagle et al., "Physical properties of oligonucleotides containing phosphoramidate-modified internucleoside linkages," NUC ACIDS RES 19:1805–1810 (1991).

Diez et al., "Unique Amino Acid Substitutions in the Capsid Proteins of Foot–and–Mouth Disease Virus from a Persistent Infection in Cell Culture," J Virol 64:5519–5528 (1990).

Fazakerley et al., "A—→ Z transition in the synthetic hexanucleotide (dCdGfl)3," FEBS 182:365–369 (1985).

Froehler et al., "Deoxynucleoside H–Phosphonate Diester Intermediates in the Synthesis of Internucleotide Phosphate Analogues," Tet Lett 27:5575–5578 (1986).

Froehler et al., "Phosphoramidate analogues of DNA: synthesis and thermal stability of heteroduplexes," Nuc Acids Res 16:4831–4839 (1988).

Froehler et al., "Synthesis of DNA via deoxynucleoside H–phosphonate intermediates," Nuc Acids Res 14:5399–5407 (1986).

Froehler et al., "The Use of Nucleoside H–Phosphonates in the Synthesis of Deoxyoligonucleotides," Nucls & Nuclt 6:287–291 (1987).

Guinosso et al., "Synthesis of the DNA Ligase–Adenylate Intermediate: Lysine (epsilon–amino)–Linked Adenosine Monophosphoramidate," NUCLS & NUCLT 10:259–262 (1991).

Haeuptle et al., "Translation arrest by oligodeoxynucleotide complementary to mRNA coding sequences yields polypeptides of predetermine length," Nuc Acids Res 14:1427–1448 (1986).

Hansch et al., "Linear Relationships between Lipophilic Character and Biological Activity of Drugs," J Pharm Sci 61:1–19 (1972).

Hobbs et al., "Palladium–Catlyzed Synthesis of Alkynylamino Nucleosides. A Universal Linker for Nucleic Acids," J Org Chem 54:3420–3422 (1989).

Hoke et al., "Effects of phosphorothioate capping on antisense oligonucleotide stability, hybridization and antiviral efficacy versus herpes simplex virus infection," Nuc Acids Res 19:5743–5748 (1991).

Huang et al., "Building Blocks for Oligonucleotide Analogues with Dimethylene Sulfide, Sulfoxide, and Sulfone Groups Replacing Phosphodiester Linkages," J Org Chem 56:3869–3882 (1991).

Huff et al. "DNA Damage at Thymine N–3 Abolishes Base–paring Capacity during DNA Synthesis," J Biol Chem 262(26):12843–12850 (1987).

Inoue et al., "Synthesis and hybridization studies on two complementary nona(2'-methyl)ribonucleotides," Nuc Acids Res 15:6131–6148 (1987).

Itoh et al, "A Novel Synthesis of 1–Deazaadenosine," Heterocycles 17:305–309 (1982).

Itoh et al, "Studies on the Chemical Synthesis of Potential Antimetabolites," NUCL & NUCLT 1(2):179–190 (1982).

Joshi et al., "Inhibition of Human Immunodeficiency Virus Type1 Multiplication by Antisense RNA Expression," J VIROL 65:5524–5530 (1991).

Kabanov et al., "A new class of antivirals: antisense oligonucleotides combined with a hydrophobic substituent effectively inhibit influenza virus reproduction and synthesis of virus–specific proteins in MDCK cells," FEBS 259:327–330 (1990).

Lieb et al., "Biological Membranes behave as Non–porous Polymeric Sheets with Respect to the Diffusion of Non–electrolytes," Nature 224:240–243 (1969).

Loke et al., "Characterization of oligonucleotide transport into living cells," PROC NATL ACAD SCI 86:3474–3478 (1989).

Manoharan et al., "Novel Functionalization of the Sugar Moiety of Nucleic Acids for Multiple Labeling in the Minor Grove," Tet Lett 32:7171–7174 (1991).

Mizuno et al, "Synthetic Studies of Potential Antimetabolites. IX. The Anomeric Configuration of Tubercidin," J Org Chem 28:3329–3331 (1963).

Montgomery et al, "A Comparison of Two Methods for the Preparation of 3–Deazapurine Ribonucleosides," J Het Chem 14:195–197 (1977).

Montgomery et al, "Analogues of Tubercidin," J Med Chem 10:665–667 (1967).

Oeller et al., "Reversible Inhibition of Tomato Fruit Senescence by Antisense RNA," Science 254:437–439 (1991).

Praseuth et al., "Sequence–specific binding and photo-crosslinking of a and b oligodeoxynucleotides to the major groove of DNA via triple–helix formation," Proc Natl Acad Sci 85:1349–1353 (1988).

Schneider et al., "Building Blocks for Oligonucleotide Analogs with Dimethylene–Sulfide, –Sulfoxide, and –Sulfone Groups Replacing Phosphodiester Linkages," TET LETT 31: 335–338 (1990).

Severin et al., "Hydrophobized Antiviral Antibodies and Antisense Oligoncleotides," ADV Enzyme Regulation 31:417–430 (1991).

Shoji et al., "Mechanism of cellular uptake of modified oligodeoxynucleotides containing methylphophonate linkages," Nuc Acids Res 19:5543–5550 (1991).

Singer et al, "Comparison of Polymerase Insertion and Extension Kinetics of a Series of 02–Alkyldeoxythymidine Triphosphates and 04–Methyldeoxythymidine Triphosphate," BIOCHEM 28:1478–1483 (1989).

Sproat et al., "Highly efficient chemical synthesis of 2'–O–methyloligoribonucleotides and tetrabiotinylated derivatives; novel probes that are resistant to degradation by RNA or DNA specific nucleases," Nuc Acids Res 17:3373–3386 (1989).

Sproat et al., "New Synthetic routes to synthons suitable for 2'–O–allyloligorbonucleotide assembly," Nuc Acids Res 19:733–738 (1991).

Tanaka et al, "Regiospecific C–Alkylation of Uridine: A Simple Route to 6–Alkyluridines," Tet Lett 19:4755–4758 (1979).

Uhlmann et al, "Antisense Oligonucleotides: A New Therapeutic Principle," Chem Rev 90:543–584 (1990).

Walter et al., "Permability of Small Nonelectrolytes through Lipid Bilayer Membranes," J Membrane Biol 90:207–217 (1986).

Wright et al, "Synthesis, Cell Growth Inhibition, and Antitumor Screening of 2–(p–n–Butylanilino)purines and Their Nucleoside Analogues," J Med Chem 30:109–116 (1987).

Yakubov et al., "Mechanism of oligonucleotdie uptake by cells: Involvement of specific receptors ?," Proc Natl Acad Sci 86:6454–6458 (1989).

| Compound | Cellular Compartment Stained | Structure* |
|---|---|---|
| 223-19C<br>1351 daltons | mitochondria | $X^1$ = fluorescein-C(O)-NH-$(CH_2)_6$-O-P(O)[NH-$(CH_2)_5CH_3$]O- 5'<br>$X^2$ = 3'-N[$(CH_2)_5CH_3$]-$CH_2$-$CH_2$-5'<br>$B^1 = B^2$ = 4-O-butylthymine |
| 223-4D<br>1834 daltons | endoplasmic reticulum and nuclear envelope | $X^1$ = fluorescein-C(O)-NH-$(CH_2)_6$-O-P(O)[NH-$(CH_2)_8$-$CH_3$]O- 5'<br>$X^2$ = 3'-O-P(O)[NH-$(CH_2)_5CH_3$]O- 5'<br>$X^3$ = 3'-O-P(O)[NH-$(CH_2)_8CH_3$]O- 5'<br>$B^1 = B^2 = B^3$ = 5-(1-pentynyl)uracil |
| 156-71A<br>1520 daltons | cytoplasm and nucleus | $X^1$ = fluorescein-C(O)-NH-$(CH_2)_6$-O-P(O)[NH-$(CH_2)_{11}CH_3$]O- 5'<br>$X^2$ = 3'-O-P(O)[NH-$(CH_2)_{11}CH_3$]O- 5'<br>$B^1 = B^2$ = 5-(1-pentynyl)uracil |
| 156-31F<br>1208 daltons | outer membrane | $X^1$ = fluorescein-C(O)-NH-$(CH_2)_6$-O-P(O)[NH-$(CH_2)_2$NHCO-3-O-cholesterol]O-5'<br>$B^1$ = thymine |

* - linkages ($X^1$, $X^2$, etc) are listed starting at the 5' position with $X^1$ linked to the 5' terminal position; all compounds contain 2'-deoxyribose and contain a free 3' hydroxyl group at the 3' terminal nucleoside residue; bases ($B^1$, $B^2$, etc) are listed starting at the 5' terminal nucleoside residue

Fig. 2A

| Compound | Cellular Compartment Stained | Structure* |
|---|---|---|
| 183-53<br>846 daltons | cytoplasm and nucleus | $X^1$ = fluorescein-C(O)-NH- 5'<br>$X^2$ = 3'-O-CH$_2$-O-5'<br>$B^1$ = $B^2$ = 4-O-methylthymine |
| 223-98E<br>2155 daltons | cytoplasm and nucleus | $X^1$ = fluorescein-C(O)-NH-(CH$_2$)$_6$-O-P(O)[NH-(CH$_2$)$_5$CH$_3$]O- 5'<br>$X^2$ = $X^3$ = $X^4$ = 3'-O-P(O)[NH-(CH$_2$)$_2$OCH$_3$]O- 5'<br>$B^1$ = $B^2$ = $B^3$ = $B^4$ = 4-O butylthymine |
| 273-21D<br>2656 daltons | cytoplasm and nucleus | $X^1$ = fluorescein-C(O)-NH-(CH$_2$)$_6$-O-P(O)[NH-(CH$_2$)$_8$-CH$_3$][NH-(CH$_2$)$_2$OCH$_3$]- 5'<br>$X^2$ = $X^4$ = $X^6$ = 3'-O-CH$_2$-O-5'<br>$X^3$ = $X^5$ = 3'-O-P(O)[NH-(CH$_2$)$_2$OCH$_3$]O- 5'<br>$B^1$ = $B^2$ = $B^3$ = $B^4$ = $B^5$ = $B^6$ = 4-O-butylthymine |
| 273-22D<br>3484 daltons | cytoplasm and nucleus | $X^1$ = fluorescein-C(O)-NH-(CH$_2$)$_6$-O-P(O)[NH-(CH$_2$)$_8$-CH$_3$]O- 5'<br>$X^2$ = $X^4$ = $X^6$ = $X^8$ = 3'-O-CH$_2$-O- 5'<br>$X^3$ = 3'-O-P(O)(O$^-$)-O- 5'<br>$X^5$ = 3'-O-P(O)[NH-(CH$_2$)$_8$CH$_3$]O- 5'<br>$X^7$ = 3'-O-P(O)[NH-(CH$_2$)$_2$OCH$_3$]O- 5'<br>$B^1$ = $B^2$ = $B^3$ = $B^4$ = $B^5$ = $B^6$ = $B^7$ = $B^8$ = 4-O-butylthymine |

* - linkages ($X^1$, $X^2$, etc) are listed starting at the 5' position with $X^1$ linked to the 5' terminal position; all compounds contain 2'-deoxyribose and contain a free 3' hydroxyl group at the 3' terminal nucleoside residue; bases ($B^1$, $B^2$, etc) are listed starting at the 5' terminal nucleoside residue

R = 1-pentynyl
Fl = fluorescein

273-22D

B = 4-O-butylthymine
Fl = fluorescein

OLIGONUCLEOTIDES AND THEIR ANALOGS CAPABLE OF PASSIVE CELL MEMBRANE PERMEATION

This is a continuation of application Ser. No. 07/868,487 filed on Apr. 14, 1992, now U.S. Pat. No. 5,633,360.

TECHNICAL FIELD

The invention relates to therapeutic and diagnostic applications of oligonucleotides, and especially to the ability of these oligonucleotides to enter cells. More specifically, the invention concerns oligonucleotides and their analogs which are capable of passive permeation of cell membranes. Having entered target cells, the oligonucleotides are free to bind nucleic acids, protein, carbohydrate, or other desired targets; if labeled, they permit visualization of the cells or subcellular compartments.

BACKGROUND ART

Therapeutic methods which utilize oligonucleotides as active agents are based on a number of end strategies. The earliest concept in this group of strategies appears to be the "antisense" approach wherein the oligonucleotide is designed to be the antisense counterpart of an mRNA transcript and is thus expected to interrupt translation of a gene which has an undesired effect in the cell. More recently, it has been found that oligonucleotides complex with duplex DNA to form triplexes in a sequence-specific manner according to what have been designated as "GT" and "CT" interaction modes. Thus, not only could mRNA transcripts serve as targets, transcription could be interrupted by targeting the duplex DNA. More recently still, it has been found possible to utilize the polymerase chain reaction (PCR) to amplify selectively oligonucleotides that empirically preferentially bind to targets of diverse molecular structure, including proteins and lipids. While the rules for sequence specificity for this type of targeting have not been elucidated (and perhaps there are none), this approach, at least in theory, permits targeting of any desired substance by the properly selected oligonucleotide. The ability to obtain specifically binding oligonucleotides in this way has expanded the possibilities for oligonucleotide therapy in that it may be possible to design oligonucleotides to target substances that reside at the cellular surface.

Nevertheless, a large number of desired targets, including all of the mRNA and double-stranded DNA targets are intracellular. A major barrier to the application of oligonucleotide therapy techniques to living systems has been the inability of oligonucleotides to cross cellular membranes. Native oligonucleotides are highly ionic, indeed negatively charged, high molecular weight materials. Such materials do not readily transit the lipophilic cell membrane.

Numerous publications have appeared that describe inhibition of gene expression by exogenously added oligomers in various cell types (Agrawal, S., et al. *Proc Natl Sci* (1988) 85:7079–7083; Uhlmann, E., et al., *Chem Revs* (1990) 90:583–584). However, oligomers added directly to cells enter the cellular cytoplasm at a low efficiency, at best, as described below. Many of the apparent sequence-specific effects that have been described are likely to be due to effects on cellular activity that do not arise from binding of the oligomer to target nucleic acid sequences in cytoplasm or nucleoplasm. In the case of RNA antisense sequences generated in situ that are complementary to a target sequence or in cell-free in vitro systems with exogenously added oligomers, gene specific effects do appear to occur by binding of the oligomer to the target sequence (Oeller, P. W., et al., *Science* (1991) 254:437–439; Joshi, S., et al., *J Virol* (1991) 65:5524–5530; Haeuptle, M.-T., et al., *Nucl Acids Res* (1986) 14:1427–1448).

It has been generally assumed that oligomers containing the native phosphodiester linkages enter cells by receptor-mediated endocytosis (Loke, S. L., et al., *Proc Natl Acad Sci USA* (1989) 86:3474–3478; Yakubov, L. A., et al., (ibid.) 6454–6458). Subsequent studies appear to show that oligomers with modified internucleotide linkages that may mitigate the presence of negative charges also enter the cells through specific receptors, rather than by passive diffusion (Akhtar, S., et al., *Nucleic Acids Res* (1991) 19:5551–5559; Shoji, Y., et al., (ibid.) 5543–5550). Entry of oligomers into cells by either receptor mediated endocytosis or by other mechanisms results in their localization into intracellular endosomes or vesicles. Thus, entry of oligomers into cellular cytoplasm or nucleoplasm is prevented by the membrane barrier surrounding these subcellular organelles (Shoji, Y. et al., (ibid) 5543–5550). Because of the low rate of such endocytosis, it has been necessary to attempt to protect the oligonucleotides from degradation in the bloodstream either by inclusion of these materials in protective transport complexes, for example with LDL or HDL (deSmidt, P., et al., *Nucleic Acids Res* (1991) 19:4695–4700) or by capping them with nuclease-resistant internucleotide linkages (Hoke, G. D., et al., (ibid.) 5743–5748).

No progress has been reported in designing oligonucleotides which are capable of passive cell membrane diffusion, so as to be able to enter cells rapidly across cellular membranes to interact with intracellular targets. Those factors related to molecular characteristics which determine the diffusion coefficients of molecules in general have, however, been extensively studied. See, for example, Stein, W. D., in "New Comprehensive Biochemistry", Vol. 2 (Membrane Transport), Elsevier/North Holland Biomedical Press (1981), pp. 1–28; Lieb, W. R., et al., *Nature* (1969) 224:240–243. It has been concluded that the distribution constant for a particular substance between the lipophilic membrane and an external aqueous phase is a direct function of the partition coefficient of the material between octanol and water times the molecular weight of the material of interest raised to an appropriate negative power characteristic of the membrane. As the appropriate negative power for, for example, red blood cells is about −4, it appears that high molecular weight substances must have hopelessly low distribution coefficients between cellular membrane and the external environment, even if their partition coefficients for octanol:water are quite high. The validity of this relationship for various small molecules, however, appears to be substantiated by experiment (Hansch, C., et al., *J Pharm Sci* (1972) 61:1–19; Walter, A., et al., *J Membrane Biol* (1986) 90:207–217).

The partition coefficient for native DNA or RNA is relatively low; less than 0.0. DNA modified by synthesis of 2-methoxyethylphosphoramidite internucleoside linkages in place of the phosphodiester linkage eliminates the negative charge associated with the internucleotide linkage, which increases the hydrophobicity of DNA. However, the octanol-water partition coefficient (Log $P_{oct}$) remains less than 0.0 (Dagle, J. M., et al., *Nucl Acids Res* (1991) 19:1805– 1810). Increased Log $P_{oct}$ values for 2-methoxyethylphosphoramidite-modified DNA were assayed by measuring the partitioning of radiolabeled DNA in an octanol-aqueous buffer system. Increased Log $P_{oct}$ was correlated with increased retention time on reversed-phase HPLC columns (Dagle, J. M., et al., *Nucl Acids Res* (1991)

19:1805–1810). Other DNA analogs, such as methylphosphonates or thioates, or DNA with lipophilic adducts (Severin, E. S., et al., *Adv Enzyme Regulation* (1991) 31:417–430) that are described in the literature are similarly expected to have Log $P_{oct}$ values less than 0.0. Oligomers containing high levels of both modified bases and internucleotide linkages have not been described.

It has now been found that by appropriate design of their molecular features, oligonucleotides can be modified from their native forms so as to permit their passive diffusion across cellular membranes, despite the high molecular weights inherent in these molecules. A standard oligonucleotide dimer with two linkage groups has a molecular weight of about 650 Daltons. The relevant factor this generates in determining distribution between membrane and aqueous medium is thus very small, which indicates that such a molecule is essentially impermeable to cell membranes. The dimers and higher molecular weight oligonucleotides of this invention are, however, capable of passive diffusion into cells. Oligonucleotide dimers, as used herein, are generally comprised of two bases and either one or two phosphodiester internucleotide linkage groups, with one linkage found between the nucleosides and a second linkage which is usually attached to the 5'-terminal hydroxyl group. Such dimers can have a third linkage attached to the 3' hydroxyl group.

The oligonucleotides of the invention, when fluorescently labeled and utilized as agents for visualizing cells or subcellular structures, are characterized by a log value of the distribution coefficient between octanol and water of about 0.0–2.5. Such oligonucleotides are capable of efficiently traversing cell membranes and have a minimum solubility in water or aqueous media of at least 10 nM, preferably 50 nM. The minimum solubility requirement is based on the minimum concentration of fluor required by current fluorescent microscopes for visualizing the label. The oligonucleotides of the invention, when utilized as (i) therapeutic agents that bind to intracellular or extracellular structures such as proteins or nucleic acids, or (ii) labeled compounds to detect or visualize cells, cell membranes or subcellular components in tissue samples, intact cells or in cell lysates, are characterized by a log value of the distribution coefficient between octanol and water of about 0.0–2.5. Such oligonucleotides also have a minimum solubility in water or aqueous media of at least about 0.001 µg/mL.

Some of the oligonucleotides of the invention were found to bind to specific subcellular components such as endoplasmic reticulum or mitochondria. Because of this, permeation-competent oligonucleotides that are fluorescently labeled can be used to directly visualize live cells or cell components in cell lysates. The aspects of the compounds that confer subcellular component-specific binding on the oligonucleotides of the invention are believed not to reside in the fluorescent moiety that is attached to the compound. However, the same oligonucleotides, either containing the fluorescent label or without the label can be synthesized utilizing, say, $^{32}P$ instead of the normal nonradioactive phosphorus isotope. Any other appropriate radiolabel can also be utilized according to conventional methods. Such radiolabeled oligonucleotides would retain their cell component-specific binding properties, but need not be directly visualized. In this case, cells or cell lysates can be specifically bound by the oligonucleotide followed by detection of bound oligonucleotide. Radiolabeled oligonucleotides used in this manner would have a minimum solubility requirement in water or aqueous media of about 0.001 µg/mL in order to be conveniently detected or quantitated by conventional methods such as scintillation counting.

DISCLOSURE OF THE INVENTION

The invention provides oligonucleotides which are at least dimers in length that are capable of efficiently traversing cell membranes in vitro and in vivo. The ability to enter cells in this manner makes the invention oligonucleotides more valuable as therapeutic compounds, and they also may be employed to visualize the interiors and location of cells by attaching the oligonucleotides to a suitable label. By assembling the design features of the invention oligonucleotides, a characterizing set of parameters may be obtained which describes oligonucleotides and their analogs having this capacity.

Thus, in one aspect, the invention is directed to an oligonucleotide capable of passive diffusion across mammalian cell membranes or any other cell membrane (plant, parasite, bacterial, yeast, viral, or fungal). The oligonucleotides of the invention are at least dimers, and are characterized by a log value of the distribution coefficient between octanol and water of about 0.0–2.5. The oligonucleotides also have a minimum solubility in water of at least 0.001 µg/mL. These partition coefficient and solubility characteristics can be conveniently measured by simple screening procedures known in the art and exemplified hereinbelow. The presence of these properties provides characterization of oligomers that are capable of the desired passive diffusion. Such oligonucleotides may be designed by modifying the structural characteristics of conventional oligonucleotides by either providing non-ionic internucleotide linkages or by providing lipophilic substitution at the base residues, or both. The combination of these modifications will be such that the required partition coefficient and solubility characteristics are obtained. In general, the oligonucleotide will contain either at least 80% of the internucleotide linkages as non-ionic modifications or at least 80% of the bases in the oligomer will be substituted with a lipophilic substituent that is preferably a hydrocarbyl group (1-8C). Hydrocarbyl groups of greater than 8 carbon atoms may also be utilized, although hydrocarbyl substituents such as C9, C10, C12, C16 or C18 will generally contribute more lipophilic character to a base than is required for permeation competence. Alternatively, some combination of these strategies may be used so that the combination of the percentage of oligonucleotide linkage substitutions and the percentage of bases with lipophilic substitutions sums to a total of 80%. This combination generally confers sufficient non-ionic character and lipophilicity on the oligonucleotide to result in a product that conforms to the required solubility and distribution coefficient values. This can be confirmed by simple assay.

By the use of appropriate lipophilic substituents, the proportion of either bases and linkages that must be modified for permeation competence can be reduced to 60% or less. In addition, the 2' position can optionally be modified with a lipophilic adduct which can reduce the proportion of bases or phosphodiester linkages that must be modified in order to retain permeation competence. The modifications that render an oligonucleotide analog permeation competent and soluble in aqueous media, as hereinbelow defined, are thus located at more than one location on the oligomer and alter the character of the oligomer with regard to its overall lipophilicity.

Preferred non-ionic internucleotide linkages include formacetal, 3'-thioformacetal, riboacetal, and amidate, triesters and thiotriesters that have pseudohydrocarbyl substituents (3-20C) as defined hereinbelow. Psuedohydrocarbyl groups are basically hydrocarbyl substituents which are permitted to contain one or more heteroatoms (including those present as substituents) representing less than 50% of the total non-hydrogen atoms in the pseudohydrocarbyl substituent. Preferred pseudohydrocarbyl moieties contain no heteroatoms. Preferred lipophilic substituents at the base residues include saturated and unsaturated straight-chain, branched-chain, or cyclic hydrocarbyl groups, such as 1-8C alkane, alkene or alkynes including ethynyl, vinyl, isopropyl, isobutyl, butynyl, butenyl, pentyl, pentenyl, isopentyl, phenethyl, methyl, ethyl, propyl, propynyl, phenyl, phenylvinyl, propenyl, butyl, pentynyl and their stereoisomers substituted at appropriate positions on the base.

It may be desirable for some applications of the oligomers of the invention to provide substitutions at the base residues that do not interfere with the capacity of the oligonucleotide to bind its target. The target may be a single-chain or duplex nucleic acid or protein or other desired substance. Appropriate substitutions for binding competent modified oligomers with target nucleic acids refer to substitutions at base positions that do not completely disrupt their capacity to hydrogen bond with complementary bases. Those positions include the N6 or C8 of adenine, the N2 or C8 of guanine, the C5 of pyrimidines, N4 of cytosine and C7 of 7-deazapurines. Synthesis of such modified bases is described in the art, as are methods for incorporation of such bases into oligonucleotides by solid-phase or solution-phase methods (Uhlmann, E., et al., *Chemical Reviews* (1990) 90:543–584, and references cited therein; pending U.S. application Ser. No. 07/787,920 U.S. Pat. No. 5,596,086 and 5,484,908. Thus, for those oligonucleotides designed to bind single-stranded or double-stranded nucleic acid targets, care must be taken to place the lipophilic substituents in such a way so as to avoid disruption of binding to the target. This is a less serious consideration in respect of oligonucleotides which are used to label cells or to bind non-nucleotide targets.

The oligonucleotides of the invention can be further modified by conjugation to label or to additional moieties, for example at the 2' positions on the sugar moieties so long as these further alterations do not disrupt the ability of the resulting oligonucleotide to diffuse across cellular membranes. Modifications of the 2' position such as 2'-O-methyl, O-ethyl, O-propyl, O-isopropyl, O-butyl, O-isobutyl, O-propenyl or O-allyl are preferred due to their increased lipophilicity compared to the 2'-hydrogen or 2'-hydroxyl found in unmodified DNA or RNA. Corresponding S-alkyl substituents may also be utilized.

In an additional aspect, the invention is directed to a method to visualize mammalian cells which method comprises contacting the cells to be visualized with at least one modified oligonucleotide of the invention (which is conjugated to label) under conditions wherein passive diffusion across the cell membrane can occur. This is followed by washing the cells to remove any oligonucleotide that has not diffused across the membrane and detecting the oligonucleotide internalized in the cells.

BRIEF DESCRIPTION OF THE DRAWINGS

FIGS. 2A, 2B and 2C show the chemical structures of oligonucleotide analogs used to visualize cells.

MODES OF CARRYING OUT THE INVENTION

Figure 1:
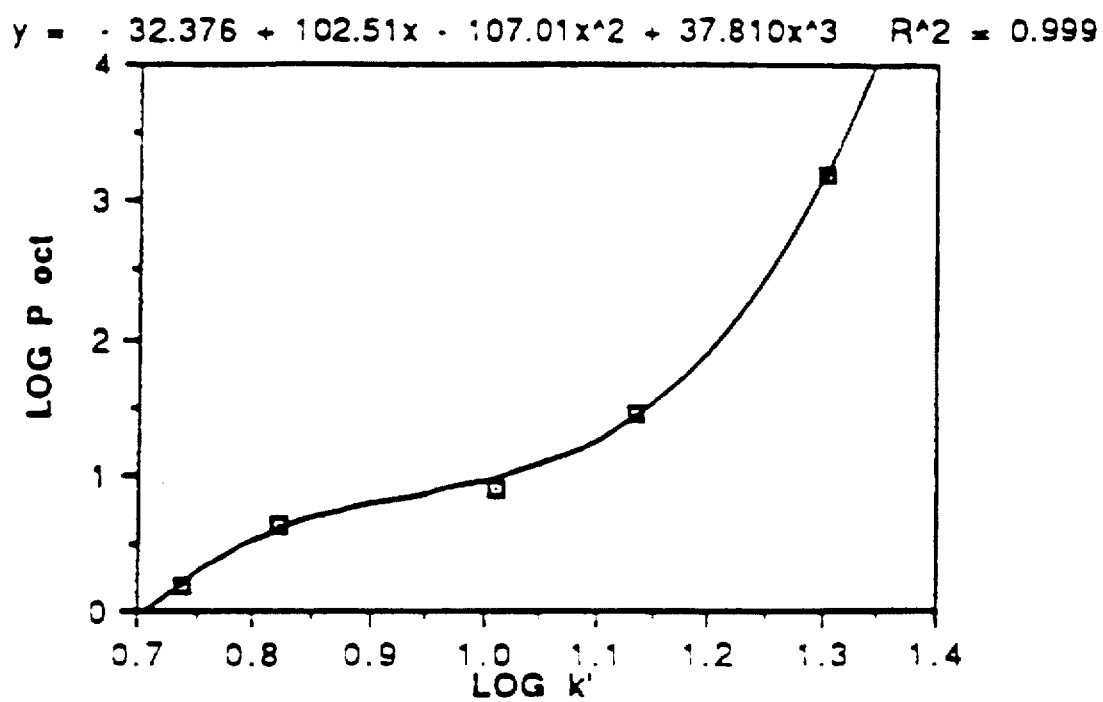
FIG. 1 shows a standard curve for the determination of partition coefficient based on retention time in RPLC.

The invention provides oligonucleotides and analogs thereof that passively diffuse across mammalian or other cell membranes. Oligonucleotides and their analogs having this property can readily be characterized by their partition coefficient and solubility properties. These oligonucleotides have a log distribution coefficient in octanol:water of about 0.0–2.5, preferably 1.0–2.2, and have a minimum solubility in water of at least 10 nM and preferably 50 nM for visualization by fluorescence microscopy and at least 0.001 µg/mL in other applications or uses. These properties are conferred by the presence of the requisite proportion of non-ionic, non-charged internucleotide linkages and of the required proportion of lipophilic substituents coupled to the base substituents of the oligonucleotide. The required characteristics of distribution coefficient and solubility can be measured by simple tests exemplified by those as follows.

Evaluation of Distribution Coefficient

The distribution coefficient need not be determined directly; that is, the distribution of the material obtained by mixing it with octanol and water and then effecting equilibrium distribution need not be evaluated. Alternate ways to measure these values take advantage of simpler techniques such as reverse-phase liquid chromatography, wherein retention times can be correlated to partition coefficient (Veith, G. D., et al., *Water Research* (1979) 13:43–47), as described in Example 1 below.

Determination of Solubility

Convenient assay methods for solubility determinations where minimal solubility is exhibited by the solute are also available. A typical procedure is set forth in Example 2.

General Parameters

As used herein "oligonucleotide" or "oligomer" is generic to polydeoxyribonucleotides (containing 2'-deoxy-D-ribose or modified forms thereof), i.e., DNA, to polyribonucleotides (containing D-ribose or modified forms thereof), i.e., RNA, and to any other type of polynucleotide which is an N-glycoside or C-glycoside of a purine or pyrimidine base, or modified purine or pyrimidine base. Oligonucleotide or oligomer, as used herein, is intended to include (i) compounds that have one or more furanose moieties that are replaced by furanose derivatives or by any structure, cyclic or acyclic, that may be used as a point of covalent attachment for the base moiety, (ii) compounds that have one or more phosphodiester linkages that are either modified, as in the case of phosphoramidate or thioate linkages, or completely replaced by a suitable linking moiety as in the case of formacetal or rioacetal linkages, and/or (iii) compounds that have one or more linked furanose-phosphodiester linkage moieties replaced by any structure, cyclic or acyclic, that may be used as a point of covalent attachment for the base moiety. Thus, the term "nucleoside," as used herein, includes compounds such as a formacetal linked "thymidine" dimer (e.g., 3' T-O-CH$_2$-O-T 5'), which does not necessarily contain a phosphorus atom.

The oligomers of the invention may be formed using conventional phosphodiester-linked nucleotides and synthesized using standard solid phase (or solution phase) oligonucleotide synthesis techniques, which are now commercially available. However, the oligomers of the invention must also contain one or more "substitute" linkages as is generally understood in the art. Most of these substitute linkages are non-ionic and contribute to the desired ability of the oligomer to diffuse across membranes. These "substitute" linkages are defined herein as conventional alternative linkages such as phosphorothioate or phosphoramidate, are synthesized as described in the generally available literature. Alternative linking groups include, but are not limited to embodiments wherein a moiety of the formula P(O)S, ("thioate"), P(S)S ("dithioate"), P(O)NR'$_2$, P(O)R', P(O)

OR⁶, CO, or CONR'₂, wherein R' is H (or a salt) or alkyl (1-12C) and R⁶ is alkyl (1-18C). Also included are alkylphosphonate linkages such as methyl-, ethyl- or propylphosphonates. Dithioate linkages are disclosed in International Publication No. WO 89/11486. Substitute linkages that may be used in the oligomers disclosed herein also include nonphosphorous-based internucleotide linkages such as the 3'-thioformacetal (—S—CH$_2$—O—), formacetal (—O—CH$_2$—O—), riboacetal and 3'-amine (—NH—CH$_2$—CH$_2$—) internucleotide linkages disclosed in commonly owned pending U.S. patent application Ser. No. 806,710 and U.S. Pat. Nos. 5,264,562 and 5,596,086, all incorporated herein by reference. Carbamate linkages disclosed in international publication number WO 86/05518 may also be used in the oligomers. One or more substitute linkages may be utilized in the oligomers in order to further facilitate binding with complementary target nucleic acid sequences or to increase the stability of the oligomers toward nucleases, as well as to confer permeation ability. Not all such linkages in the same oligomer need be identical.

The term "nucleoside" or "nucleotide" is similarly generic to ribonucleosides or ribonucleotides, deoxyribonucleosides or deoxyribonucleotides, or to any other nucleoside which is an N-glycoside or C-glycoside of a purine or pyrimidine base, or modified purine or pyrimidine base. Thus, the stereochemistry of the sugar carbons may be other than that of D-ribose in one or more residues. Also included are oligonucleotide-like compounds or analogs where the ribose or deoxyribose moiety is replaced by an alternate structure such as the 6-membered morpholino ring described in U.S. Pat. No. 5,034,506 or where an acyclic structure serves as a scaffold that positions the base or base analogs in a manner that permits efficient binding to target nucleic acid sequences or other targets. Oligonucleotide-like compounds with acyclic structures in place of the sugar residue and/or the linkage moiety are specifically intended to include both (i) structures that serve as a scaffold that positions bases or base analogs in a manner that permits efficient sequence-specific binding to target nucleic acid base sequences and (ii) structures that do not permit efficient binding or hybridization with complementary base sequences. Elements ordinarily found in oligomers, such as the furanose ring or the phosphodiester linkage may be replaced with any suitable functionally equivalent element.

As the α anomer binds to duplexes in a manner similar to that for the β anomers, one or more nucleotides may contain this linkage or a domain thereof. (Praseuth, D., et al., *Proc Natl Acad Sci* (USA) (1988) 85:1349–1353). Modifications in the sugar moiety, for example, wherein one or more of the hydroxyl groups are replaced with halogen (such as fluorine), aliphatic groups, or functionalized as ethers, amines, and the like, are also included.

"Nucleoside" and "nucleotide" include those moieties which contain not only the natively found purine and pyrimidine bases A, T, C, G and U, but also modified or analogous forms thereof. Modifications include alkylated purines or pyrimidines, acylated purines or pyrimidines, or other heterocycles. Such "analogous purines" and "analogous pyrimidines" are those generally known in the art, many of which are used as chemotherapeutic agents. An exemplary but not exhaustive list includes pseudoisocytosine, N⁴,N⁴-ethanocytosine, 8-oxy-N⁶-methyladenine, 4-acetylcytosine, 5-(carboxyhydroxylmethyl) uracil, 5-fluorouracil, 5-bromouracil, 5-carboxymethylaminomethyl-2-thiouracil, 5-carboxymethylaminomethyl uracil, dihydrouracil, inosine, N⁶-isopentenyl-adenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N⁶-methyladenine, 7-methylguanine, 5-methylaminomethyl uracil, 5-methoxy aminomethyl-2-thiouracil, 5'-methoxycarbonylmethyluracil, 5-methoxyuracil, 2-methylthio-N⁶-isopentenyladenine, uracil-5-oxyacetic acid methyl ester, pseudouracil, 2-thiocytosine, 5-methyl-2-thiouracil, 2-thiouracil, 4-thiouracil, inosine, xanthine, hypoxanthine, 5-ethyluracil, 5-ethynyluracil, 5-iodocytosine, 5-bromovinyluracil, 5-propyluracil, 5-propenyluracil, 5-trifluoromethyluracil, 5-propynyluracil, 5-propynylcytosine, 5-iodocytosine, 2-aminopurine, 3-deazaadenine, 7-deazaadenine, 3-deazaguanine, 7-deazaguanine, 7-deazaxanthosine, 8-azaadenine-6-hydroxylaminopurine, 6-thiopurine, 6-thioguanine, queosine, 2-thiocytosine, and 2,6-diaminopurine. The oligomers of the present invention may be of any length, but are at least dimers. Lengths of 2 to 28 nucleotides are preferred. However, the longer oligonucleotides may also be made, particularly those of greater than 28 nucleotides or greater than 50 nucleotides.

Also included are "derivatives" of oligonucleotides. "Derivatives" of the oligomers include those conventionally recognized in the art. For instance, the oligonucleotides may be covalently linked to various moieties such as intercalators, substances which interact specifically with the minor groove of the DNA double helix and other arbitrarily chosen conjugates, such as labels (radioactive, fluorescent, enzyme, etc.). These additional moieties may be derivatized through any convenient linkage. For example, intercalators, such as acridine can be linked through any available —OH or —SH, e.g., at the terminal 5' position of RNA or DNA, the 2' positions of RNA, or an OH, NH$_2$, COOH or SH engineered into the 5 position of pyrimidines, e.g., instead of the 5 methyl of thymine, a derivatized form which contains, for example, —CH$_2$CH$_2$NH$_2$, —CH$_2$CH$_2$CH$_2$OH or —CH$_2$CH$_2$CH$_2$SH in the 5 position. A wide variety of substituents can be attached, including those bound through conventional linkages. The indicated —OH moieties in the oligomers may be replaced by phosphonate groups, protected by standard protecting groups, or activated to prepare additional linkages to other nucleotides, or may be bound to the conjugated substituent. The 5' terminal OH may be phosphorylated; the 2'-OH or OH substituents at the 3' terminus may also be phosphorylated. The hydroxyls may also be derivatized to standard protecting groups.

Oligonucleotides or the segments thereof of are conventionally synthesized. Methods for such synthesis are found, for example, in Froehler, B., et al., *Nucleic Acids Res* (1986) 14:5399–5467; *Nucleic Acids Res* (1988) 16:4831–4839; *Nucleosides and Nucleotides* (1987) 6:287–291; Froehler, B., *Tetrahedron Letters* (1986) 27:5575–5578. Other conventional methods may be used to synthesize the oligomers or segments thereof, including methods employing phosphoramidite chemistry and/or methods that utilize solution phase synthesis.

In addition to employing these very convenient and now most commonly used, solid phase synthesis techniques, oligonucleotides may also be synthesized using solution phase methods such as triester synthesis. These methods are workable, but in general, less efficient for oligonucleotides of any substantial length.

The basic "unmodified" oligomers of the invention have the formula:

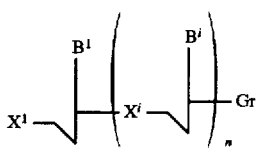 (1)

wherein

represents the ribose or deoxyribose furanose ring; in which

represents the 5' carbon and

indicates linkage to the 3' carbon
n is an integer of 1-any desired length;
i represents the ith substituent wherein i=n+1.
$X^1$ is —OH, —$OPO_3^=$, or Gr, wherein Gr is a blocking group;
$X^i$ is

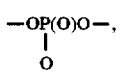

and $B^1$ and each $B^i$ is independently a purine or pyrimidine base (A, T, U, G, or C) without the hydrocarbyl substitution of the invention.

As used herein, "blocking group" refers to a substituent other than OH that is conventionally coupled to oligomers or nucleosides, either as a protecting group, an activated group for synthesis or other conventional conjugate partner such as a solid support, label, immunological carrier and the like. Suitable protecting groups are, for example, DMT or MMT; suitable activated groups are, for example, H-phosphonate, methyl phosphonate, methylphosphoramidite or β-cyanoethylphosphoramidite. Gr may also comprise a solid support. In general, the nucleosides and oligomers of the invention may be derivatized to such "blocking groups" as indicated in the relevant formulas.

Using the above formula 1 as a reference, the invention oligonucleotides can be modified in at least two respects. In one approach, at least 80% of the internucleotide linkages are modified so as to be non-ionic. In the case of dimers (n=1), there is only 1 internucleotide linkage, and this must be in the modified form. For trimers there are 2 internucleotide linkages; for tetramers there are 3, and so forth. Thus, all internucleotide linkages must be converted to non-ionic forms for oligomers which are less than hexamers. For hexamers, having 5 internucleotide linkages, only 4 of these need to be non-ionic.

Conversion of the internucleotide linkage to a non-ionic form is effected in two general ways—derivatization of the phosphodiester, phosphorothioate, or phosphoramidate linkage to a lipophilic derivative by derivatization to a lipophilic moiety, such as alkyl or unsaturated hydrocarbyl(3-20C) or alternatively, substitution of the phosphorous-based linkage by an inherently non-ionic linkage such as formacetal. Other preferred linkages include riboacetal, 5' ether —($CH_2CH_2O$)— or 3'-thioformacetal as described in pending application no. 806,710, U.S. Pat. Nos. 5,264,562 and 5,596,086.

In addition, any phosphate present at the 5' or 3' terminus of the oligonucleotide must be derivatized, for example, by further esterification to a lipophilic group containing at least 3C. A particularly useful derivatizing group may contain a label as well, for example, a fluorescent label such as fluorescein, rhodamine, or dansyl. Thus, useful derivatizing groups include Fl CONH $(CH_2)_6$— and Rh—CONH $(CH_2)_6$—, wherein Fl and Rh signify fluorescein and rhodamine, respectively.

In the alternative to replacing of at least 80% of the internucleotide linkages with non-ionic forms thereof, at least 80% of the bases associated with the nucleotides in the oligomer must contain lipophilic substitutions, including pseudohydrocarbyl groups, and preferably hydrocarbyl groups of 1-8C. Substitution may be made at any convenient position—e.g., the 5-position of pyrimidine, at the 4-O position of thymine, or at the N6 and C8 positions of adenine and N2 or C8 of guanine. Corresponding positions in non-native bases may also be used. Preferred substituted nucleosides include 5-ethynyl-dU, 5-ethynyl-dC, 8-ethynyl-dG, 5-vinyl-dU, 5-ethyl-dU, 8-ethynyl-dA, 8-propynyl-dG, 8-propynyl-dA, 5-pentyl-dU, 5-pentynyl-dU, 5-phenethyl-dU, 5-pentyl-U, 5-pentynyl-U, 5-benzyl-dC, $N^6$-methyl-8-oxo-2'-deoxy-A (MODA), 4-O-butyl-T, 5-propynyl-dC and 5-propynyl-dU.

Appropriate substitutions for binding competent modified oligomers refer to substitutions at base positions that do not completely disrupt their capacity to hydrogen bond with complementary bases. Those positions include the N6 or C8 of adenine, the N2 or C8 of guanine, the C5 of pyrimidines, N4 of cytosine and C7 of 7-deaza-purines.

As used herein, pseudohydrocarbyl substituents refers to alkyl, alkenyl, alkynyl or aromatic groups that may contain one or more heteroatoms. Preferred heteroatoms are nitrogen, oxygen and sulfur. Generally speaking, pseudohydrocarbyl substituents that facilitate passive diffusion decrease the polarity/increase the lipophilicity of the parent molecule and do not carry any charged atoms or groups.

Typical oligonucleotides of the invention also have the formula

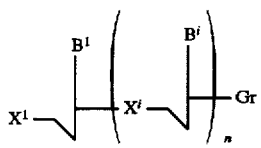 (1)

wherein

represents the ribose or deoxyribose furanose ring; in which

represents the 5' carbon and

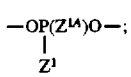

indicates linkage to the 3' carbon
n is an integer of 1-any desired length; and
i represents the ith substituent wherein i=n+1, but wherein:
$X^1$ is —OH, —$OPO_3^{-2}$, —$NR_2$ or $$-OP(Z^{1A})O-; \\ \quad | \\ \quad Z^1$$

each $X^i$ is independently $$-OP(O)O-, -YCH_2-Y-, \\ \quad | \\ \quad Z^i$$

$$-(CH_2)_m-N- \text{ or } -N-(CH_2)_m- \\ \quad\quad\quad | \quad\quad\quad\quad\quad | \\ \quad\quad\quad R \quad\quad\quad\quad\quad R$$

wherein each $Z^1$, $Z^{1A}$ and $Z^i$ is independently OH, SH, NHR (or their salts), alkyl(1-10C), —O-alkyl(1-10C), —O-allyl(1-10C), and R is H or alkyl (1-6C); and each $B^1$ and $B^i$ is independently a purine or pyrimidine base optionally containing a hydrophobic substituent with the proviso that at least 80% of the $X^i$ must be other than

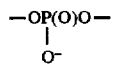

$$-OP(O)O- \\ \quad | \\ \quad O^-$$

or at least 80% of $B^1+B^i$ must contain a hydrophobic substituent, or both the internucleoside linkages and bases are modified as described so that the sum of said modifications comes to 80%. A fully substituted oligomer would consist of linkage and base modifications that sums to 200%.

By way of example, therefore, the oligomers of the invention must have, for example, none of the internucleoside linkages modified but 80% of the bases will contain a hydrophobic substituent, or none of the bases may contain a hydrophobic substituent if 80% of the internucleotide linkages are substituted as described above, or the oligomer may contain 40% modified internucleotide linkages and have 40% of the bases substituted with a hydrophobic substituent, or the oligomer may contain 10% of the oligonucleotide linkages modified while 70% of the bases contain hydrophobic substituents and so forth.

The foregoing restrictions are an attempt to set an arbitrary criterion for workable compounds. Of course, no absolute criterion of this type can be perfect, since the use of more hydrophobic substitutions may decrease the percentages required while modifying the oligonucleoside as described above, but with less hydrophobic substituents may require that more substitutions be made. However, for the types of substitutions described herein, it appears that, at a minimum, 80% of either the type of substitution will be sufficient or some division of substitutions between these two possibilities that sums to 80% will be satisfactory.

In addition to the required modifications set forth above, the oligonucleotides of the invention may optionally be further modified to enhance other desired properties such as binding strength, nuclease resistance, presence of label, and the like. Included among such modifications are the inclusion of a covalently binding moiety to enhance the stability of binding to target; the inclusion of at least one region of inverted polarity to enhance ability to form triple helices; and modification at the 2'-position to provide additional hydrophobicity and to enhance binding. A brief description of these modifications follows:

Covalent Bonding Moiety

Included in some of the oligomers of the invention, in addition to the required permeability-conferring substitutions, is a moiety which is capable of effecting at least one covalent bond between the oligomer and the duplex. Multiple covalent bonds can also be formed by providing a multiplicity of such moieties. The covalent bond is preferably to a base residue in the target strand, but can also be made with other portions of the target, including the saccharide or phosphodiester. The reaction nature of the moiety which effects crosslinking determines the nature of the target in the duplex. Preferred crosslinking moieties include acylating and alkylating agents, and, in particular, those positioned relative to the sequence specificity-conferring portion so as to permit reaction with the target location in the strand.

The crosslinking moiety can conveniently be placed as an analogous pyrimidine or purine residue in the sequence of the oligomer. The placement can be at the 5' and/or 3' ends, the internal portions of the sequence, or combinations of the above. Placement at the termini to permit enhanced flexibility is preferred. Analogous moieties can also be attached to peptide backbones.

In one preferred embodiment of the invention, a switchback oligonucleotide containing crosslinking moieties at either end can be used to bridge the strands of the duplex with at least two covalent bonds. In addition, nucleotide sequences of inverted polarity can be arranged in tandem with a multiplicity of crosslinking moieties to strengthen the complex.

Exemplary of alkylating moieties that are useful in the invention include $N^4$ $N^4$-ethanocytosine and $N^6$ $N^6$-ethanoadenine.

Inverted Polarity

The "unmodified" oligomer and its modified form may also contain regions of inverted polarity. In their most general form, inverted polarity oligonucleotides, contain at least one segment along their length of the formula:

$$3'\text{-----}{\rightarrow}5'\text{--C--}5'\text{-----}3' \quad\quad (1)$$

$$5'\text{-----}{\rightarrow}3'\text{--C--}3'\text{-----}5' \quad\quad (2)$$

where -C- symbolizes any method of coupling the nucleotide sequences of opposite polarity.

In these formulas, the symbol 3'----5' indicates a stretch of oligomer in which the linkages are consistently formed between the 5' hydroxyl of the ribosyl residue of the nucleotide to the left with the 3' hydroxyl of the ribosyl residue of the nucleotide to the right, thus leaving the 5' hydroxyl of the rightmost nucleotide ribosyl residue free for additional conjugation. Analogously, 5'----3' indicates a stretch of oligomer in the opposite orientation wherein the linkages are formed between the 3' hydroxyl of the ribosyl residue of the left nucleotide and the 5' hydroxyl of the ribosyl residue of the nucleotide on the right, thus leaving the 3' hydroxyl of the rightmost nucleotide ribosyl residue free for additional conjugation.

The linkage, symbolized by -C-, may be formed so as to link the 5' hydroxyls of the adjacent ribosyl residues in formula (1) or the 3' hydroxyls of the adjacent ribosyl residues in formula (2), or the "-C-" linkage may conjugate other portions of the adjacent nucleotides so as to link the inverted polarity strands. "-C-" may represent a linker moiety, or simply a covalent bond.

It should be noted that if the linkage between strands of inverted polarity involves a sugar residue, either the 3' or 2' position can be involved in the linkage, and either of these positions may be in either R or S configuration. The choice of configuration will in part determine the geometry of the oligomer in the vicinity of the linkage. Thus, for example, if adjacent 3' positions are used to effect a covalent linkage, less severe deformation of the oligonucleotide chain will generally occur if both 3' hydroxyls involved in the linkage are in the conventional R configuration. If they are both in the S configuration, this will result in a favorable "kink" in the chain.

In addition to the use of standard oligonucleotide synthesis techniques or other couplings to effect the 5'-5' or 3'-3' linkage between ribosyl moieties, alternative approaches to joining the two strands of inverted polarity may be employed. For example, the two appended bases of the opposing termini of the inverted polarity oligonucleotide sequences can be linked directly or through a linker, or the base of one can be linked to the sugar moiety of the other. Any suitable method of effecting the linkage may be employed. The characterizing aspect of the switchback oligonucleotides of the invention is that they comprise tandem regions of inverted polarity, so that a region of 3'→15' polarity is followed by one of 5'→3' polarity, or vice versa, or both.

Depending on the manner of coupling the segments with inverted polarity, this coupling may be effected by insertion of a dimeric nucleotide wherein the appropriate 3' positions of each member of the dimer or the 5' positions of each member of the dimer are activated for inclusion of the dimer in the growing chain, or the conventional synthesis can be continued but using for the condensing nucleotide a nucleotide which is protected/activated in the inverse manner to that which would be employed if the polarity of the chain were to remain the same. This additional nucleotide may also contain a linker moiety which may be included before or after condensation to extend the chain.

The synthesis of oligonucleotides having modified residues and/or inverted polarity may be accomplished utilizing standard solid phase synthesis methods.

A particularly preferred dimer synthon used to mediate the switchback in an oligomer is the o-xyloso linker. The o-xyloso linker consists of two xylose-nucleosides linked to each other through o-xylene at the 3' position of each xylose sugar. This switchback linker synthon can be synthesized using α,α'-dibromoxylene and 5'-DMT xylose nucleoside. The dimer can then be converted to the H-phosphonate and used in solid phase synthesis to generate oligomers.

Switchback linkers are relatively hydrophobic and are thus suitable for incorporation into the permeation-competent oligomers described herein. Such linkers may be incorporated into oligomers that are binding competent relative to complementary nucleic acid targets or oligomers that are not binding competent.

2' Modified Oligomers

Included in some of the oligomers containing C-5 modified pyrimidines of the invention are modifications of the ribose or deoxyribose sugar. 2'-O-methyl-, 2'-O-ethyl- and 2'-O-allyloligo-ribonucleotides have been synthesized and shown to bind to single-stranded complementary nucleic acid sequences (Cotten, M., et al., *Nucleic Acids Res* (1990) 19:2629–2635; Blencowe, B. J., et al., *Cell* (1989) 59:531–539; Sproat, B. S., et al., *Nucleic Acids Res* (1989) 17:3373–3386; Inoue, H., et al., *Nucleic Acids Res* (1987) 15:6131–6148; Morisawa, H., et al., European Patent Publication No. 0339842; Chavis, C., et al., *J Organic Chem* (1982) 47:202–206; Sproat, B. S., et al., *Nucleic Acids Res* (1991) 19:733–738). The 2'-modified oligomers were reported to be relatively nuclease stable compared to unmodified controls (Guinosso, C. J., et al., *Nucleosides and Nucleotides* (1991) 10:259–262). Synthesis of 2'-fluoro nucleosides and their incorporation into oligonucleotides has also been described (Codington, J. F., et al., *J Org Chem* (1964) 29:558–564; Fazakerley, G. V., et al., *FEBS Lett* (1985) 182:365–369). Synthesis of oligonucleotide analogs containing the modified bases described herein would be based on methods described.

Synthesis of 2'-thioalkyl nucleosides is accomplished as described in pending U.S. application Ser. No. 07/799,824.

Utility and Administration

As the oligonucleotides of the invention are capable of passive diffusion across cell membranes they can be used to visualize and label cells. For this use, the oligonucleotides of the invention are provided with a detectable label, such as a radiolabel, fluorescent label, chromogenic label, enzyme label, and the like, and are contacted with the preparation of cells to be visualized. After a suitable incubation period of about 15 minutes to 2 hours at about 25° to 35° C. the solution containing the labeled oligonucleotides is removed and the cells are washed to remove any unincorporated oligonucleotide. The cells are then formatted for visualization by fluorescence microscopy and detected by visualization of the labeled oligonucleotide.

For example, for a fluorescent labeled oligonucleotide, the cells can be plated on a microscope slide and visualized directly.

In addition to employing the oligonucleotides of the invention to visualize cells, the oligonucleotides of the invention are useful in therapy and diagnosis.

Those oligonucleotides that are capable of significant single-stranded or double-stranded target nucleic acid binding activity to form duplexes, triplexes or other forms of stable association, or which bind specific target substances, such as proteins, are useful in diagnosis and therapy of conditions that are associated with these targets. For example, one or more genes associated with viral infections due to say, HIV, HCMV, HSV or HPV may be targeted. Other therapeutic applications may employ the oligomers to specifically inhibit the expression of genes that are associated with the establishment or maintenance of a pathological condition, such as those for adhesion molecules, receptor molecules or oncogenes that may be associated with inflammatory conditions, immune reactions or cancer respectively. Diagnostic applications for the oligomers include their use as probes for detection of specific sequences by any standard method.

In therapeutic applications, the oligomers are utilized in a manner appropriate for treatment of, for example, viral infections or malignant conditions. For such therapy, the oligomers can be formulated for a variety of modes of administration, including systemic, topical or localized administration. Techniques and formulations generally may be found in *Remington's Pharmaceutical Sciences*, Mack Publishing Co., Easton, Pa., latest edition. The oligomer active ingredient is generally combined with a carrier such as a diluent or excipient which may include fillers, extenders, binders, wetting agents, disintegrants, surface-active agents, or lubricants, depending on the nature of the mode of administration and dosage forms. Typical dosage forms include tablets, powders, liquid preparations including suspensions, emulsions and solutions, granules, capsules and suppositories, as well as liquid preparations for injections, including liposome preparations.

For systemic administration, injection is preferred, including intramuscular, intravenous, intraperitoneal, and subcutaneous. For injection, the oligomers of the invention are formulated in liquid solutions, preferably in physiologically compatible buffers such as Hank's solution or Ringer's solution. In addition, the oligomers may be formulated in solid form and redissolved or suspended immediately prior to use. Lyophilized forms are also included. Dosages that may be used for systemic administration preferably range from about 0.01 mg/Kg to 50 mg/Kg administered once or twice per day. However, different dosing schedules may be utilized depending on (i) the potency of an individual oligomer at inhibiting the activity of its target gene, (ii) the severity or extent of a pathological disease state associated with a given target gene, or (iii) the pharmacokinetic behavior of a given oligomer.

Systemic administration can also be by transmucosal or transdermal means, or the compounds can be administered orally. For transmucosal or transdermal administration, penetrants appropriate to the barrier to be permeated are used in the formulation. Such penetrants are generally known in the art, and include, for example, bile salts and fusidic acid derivatives for transmucosal administration. In addition, detergents may be used to facilitate permeation. Transmucosal administration may be through use of nasal sprays, for example, or suppositories. For oral administration, the oligomers are formulated into conventional oral administration forms such as capsules, tablets, and tonics.

For topical administration, the oligomers of the invention are formulated into ointments, salves, gels, or creams, as is generally known in the art.

In addition to use in therapy, the oligomers of the invention may be used as diagnostic reagents to detect the presence or absence of the target substances to which they specifically bind. Such diagnostic tests are conducted by complexation with the target which complex is then detected by conventional means. For example, the oligomers may be labeled using radioactive, fluorescent, or chromogenic labels and the presence of label bound to solid support detected. Alternatively, the presence of complexes may be detected by antibodies which specifically recognize them. Means for conducting assays using such oligomers as probes are generally known.

In addition to the foregoing uses, the ability some of the oligomers to inhibit gene expression can be verified in in vitro systems by measuring the levels of expression in recombinant systems.

The following examples are intended to illustrate but not to limit the invention.

EXAMPLE 1

Evaluation of Distribution Coefficient

When a compound is allowed to partition between octanol and water, the concentration of the compound in the octanol divided by the concentration of the compound in the water is commonly referred to as the octanol/water partition coefficient ($P_{oct}$). This number and the logarithm of the partition coefficient (Log $P_{oct}$) are useful parameters when describing the permeability of a compound towards its membrane. A modification of the procedure of Veith, G. D., Austin, N. M., and Morris, R. T., *Water Research* (1979) 13:43–47 using the HPLC retention time of compounds was used to determine the log of the partition coefficients of oligonucleotides (Log $P_{oct}$). Essentially, the partition coefficients for compounds with unknown Log $P_{oct}$ may be determined by comparison of retention times of the desired compounds with compounds of known Log $P_{oct}$. The HPLC retention times of a set of standard compounds having known Log $P_{oct}$ values was used to generate a plot of Log $P_{oct}$ versus Log k', where k'=[$t_r$-$t_o$]/$t_o$. (Here $t_r$=retention time, and $t_o$=void time). The resulting plot was fit to a third degree polynomial curve using Cricket Graph software. A typical equation for the curve was y=32.376+102.51x−107.0$x^2$+37.810$x^3$. Typical $R^2$ values were $R^2$=0.999.

The column used was a Hamilton PRP-1, 10 micron, 150×4.6 mm ID column. Solvent buffers used were: Solution A: 5 mM potassium phosphate in 2% $CH_3CN$ in $H_2O$, pH=7.4, and Solution B: 85% $CH_3CN$ in $H_2O$. A flow rate of 1 mL/min was used. A linear gradient was used that went from 0% to 100% solution B in 30 min. Detection was monitored at 254 and 500 nanometers. Stock solutions of five standards were made up as 100 OD (A260 units)/mL solutions in 50% aqueous $CH_3CN$. Then 10 OD (A260)/mL solutions were made from the stock solutions by dilution with $H_2O$. Void times (to) were calculated by injecting MeOH and monitoring for the first baseline disturbance. These values were typically k'=1.45 min.

The five standard compounds used for the determination of the curve were 3-aminophenol (Log $P_{oct}$=0.17), 2-aminophenol (Log $P_{oct}$=0.62), aniline (Log $P_{oct}$=0.9), o-nitroaniline (Log $P_{oct}$=1.44), and benzophenone (Log $P_{oct}$=3.18). The Log $P_{oct}$ values for these compounds were discussed in the paper of Veith et al. above. The five samples were mixed in a 1:1:1:1:3 proportion. Aliquots of 20–50 microliters of this mixture were injected. Their resulting retention times and known Log $P_{oct}$ values were used to generate a curve as described above. Samples with an unknown Log $P_{oct}$ were made up as solutions of 5 OD (A260)/mL in MeOH. Aliquots of 20–40 microliters were injected. A typical standard curve is shown for the five standard reference compounds in FIG. 1. The retention time was used to calculate a k' value. This k' value and the standard curve were then used to determine the Log $P_{oct}$ value for unknown compounds.

EXAMPLE 2

Determination of Solubility of Oligonucleotide Analogs

Oligonucleotides were resuspended in water at a stock concentration of 10 μM to 10 mM. The solution was then diluted in the aqueous media such as DMEM tissue culture medium at decreasing concentrations. The microscope was then used to analyze the solution for fine particles, micelles, etc. Solubility was detected at a minimum oligomer concentration of 50 nM. This lower solubility limit was determined by the sensitivity of the fluorescent microscope. This value can be extended to a 10 nM concentration using more sensitive apparatus.

EXAMPLE 3

Cell staining protocol

Oligonucleotides with various base or backbone modifications were synthesized with one of a variety of amino-linkers. These linkers included "5'-amino-modifier C6" (Glen Research; cat. no. 10-1906), "amino-modifier dT" (Glen Research; cat. no. 10-1039), and "3'-amino-modifier CPG" (Glen Research; cat. no. 20-2950). The following fluors were linked to the oligomers to monitor uptake: tetramethylrhodamine, resorufin, fluorescein, BODIPY (Molecular Probes) and acridine. A number of other fluors including dansyl, various coumarins, bimane, and pyrene have been evaluated as potential fluorescent probes, however these did not have a bright enough signal (relative quantum yield) to enable further investigation. A preferred fluor is fluorescein. This dye is itself permeant to most of the cell types tested, giving a total cellular fluorescence. Within 15 min after washing the dye away from the exterior of the cells, the intracellular pool of the dye is pumped out, either by an organic anion pump mechanism or by diffusion. Fluorescein was conjugated to all of the linkers (without oligonucleotide) used and these conjugates were shown to retain the same biological properties. This fluor is very fluorescent, it does however quench rapidly. It is also pH sensitive, being greater than an order of magnitude less fluorescent at pH 5.0 than at pH 7.5. At pH 5.0 the molecule has a net neutral charge, at pH 7.5 it has a net negative charge. BODIPY, which has desirable molecular characteristics such as a neutral charge at cellular pH ranges, lower molecular weight than fluorescein and a greater quantum yield than fluorescein is also a preferred fluor.

Fluorescent measurements were made using a Zeiss Axiovert 10 microscope equipped with a 50 W mercury arc lamp and outfitted with a set of fluorescent filters available from Omega Optical (Burlingtion, Vt., USA). Observations were made from live cells with a 63x or 100x objective (culture chamber and conditions described below). Photographs were taken with Tri-X/ASA 400 Kodak film and developed with Diafine developer (ASA rating 1600). Exposure time was fixed at 15 to 60s to enable direct comparison.

Fluorescent measurements were also made using a Nikon Diaphot inverted microscope equipped with a phase 4 long working distance condensor, 100 W mercury arc lamp, Omega optical fluorescent filters, 40x, 60x and 100x PlanApochromat phase/oil-immersion objectives, and 100% transmission to the video port. A Quantex high-intensity/intensified CCD camera was used to digitize the fluorescent information. This information was sent to a Data Translations FrameGrabber board mounted on a Macintosh II CPU. The Macintosh II was equipped with 8 MB RAM and had attached to it a 330 MB hard drive. Images were recorded using public domain NIH software "IMAGE". Linearity of information was established using a series of neutral density filters. Relative fluorescent intensity was compared between samples using the same camera settings and variable neutral density filters.

Optimal fluorescence measurements were made using a confocal microscope imaging system which optically slices "sections" through a cell. A Noran real-time confocal imaging optical path equipped with a 3-line (457 nm, 488 nm, 529 nm) laser which is hooked up to the Zeiss Axiovert 10 inverted microscope described above was used. The imaging system was the Macintosh II system described above.

The cell staining assay utilized various cell lines and included P388D1 (mouse macrophage), HEPG2 (human liver), CV1 (monkey epithelial), ccd50sk (untransformed human fibroblast), Rat2 (rat fibroblast), MDCK (kidney cells), L6 (rat myoblast), L cells (mouse fibroblast), HeLa (human adenocarcinoma), skov3 (human ovarian adenocarcinoma), and skbr3 (human breast adenocarcinoma) cells. Other cell lines that were used included Jurkat (human T cell), H9 (human T cell), NIH3T3 (mouse fibroblast), HL60 (human T cell), and H4 (rat liver). All cell lines are commercially available from the American Type Culture Collection, Rockville, Md.

Cells were grown on 25 mm-#1 coverslips in media containing 25 mM HEPES, pH 7.3, (which helps maintain pH on the microscope) without phenol red (which can lead to high background fluorescence when working with living cells). Coverslips were used so that the high numerical aperture oil-immersion lenses on the microscope could be used. The coverslips were mounted onto "viewing chambers": 6-well petri dishes which have 22 mm holes drilled into the bottom. The slides were mounted with silicon vacuum grease which was shown to be non-toxic to the cells. 12×12 mm glass rasching rings (Stanford Glassblowing Laboratory, Stanford, Calif.) were mounted directly onto the coverslip using paraffin wax. The chamber permitted the use of incubation volumes less than 200 μL. Fluorescent oligonucleotide conjugates were added at concentrations ranging from 0.1 to 150 μM. Stock concentrations of oligonucleotides were prepared in 25 mM HEPES, pH 7.3. Oligonucleotides were added to media with or without 10% 4 hr-heat inactivated (56° C.) fetal bovine serum.

Incubation times ranged from 15 minutes to 24 h. 2 hour incubations were generally utilized for cell staining. Cells were then extensively washed to remove extracellular oligomer using media and observed at room temperature. Slides were optionally replaced in the incubator and were observed over the following 48–72 h.

EXAMPLE 4

Subcellular Compartment Staining

Fluorescent oligomer compounds were placed on fibroblasts, hepatocytes, muscle and carcinoma cell lines at 50 μM for 2 hours at 37° C.; the cells were washed with cell media and live cells were visualized for cellular staining using fluorescent confocal microscopy. The results obtained for representative compounds were:

| Compound | Log $P_{oct}$* | Cellular Compartment Stained |
| --- | --- | --- |
| 223-19C | ND | Mitochondria |
| 183-53 | 0.26 | Cytoplasmic/nucleus |
| 223-4D | 1.61 | Endoplasmic reticulum/nuclear envelope |
| 156-71A | 2.09 | Cytoplasmic/nucleus |
| 156-31F | ND | Outer membrane |
| 223-98E | 1.14 | Cytoplasmic/nucleus |
| 273-21D | 1.86 | Cytoplasmic/nucleus |
| 273-22D | 2.18 | Cytoplasmic/nuclear stain |

*Log $P_{oct}$ at pH 7.4; ND, not determined

Figure 2C:
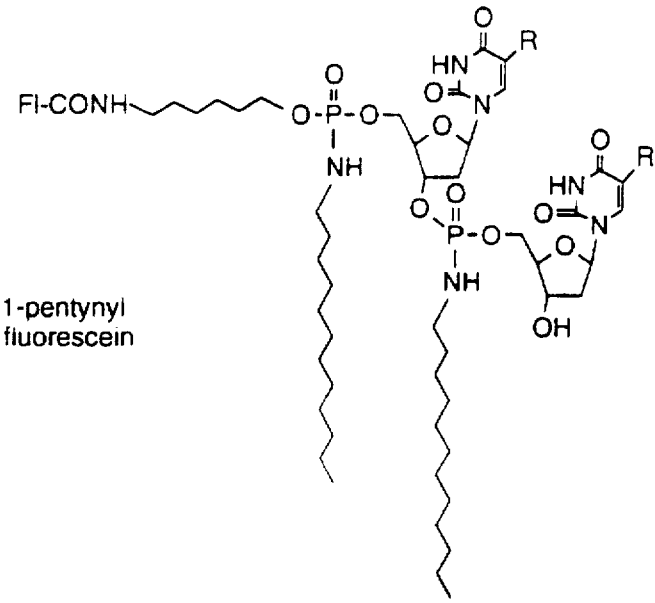
Figure 2C:
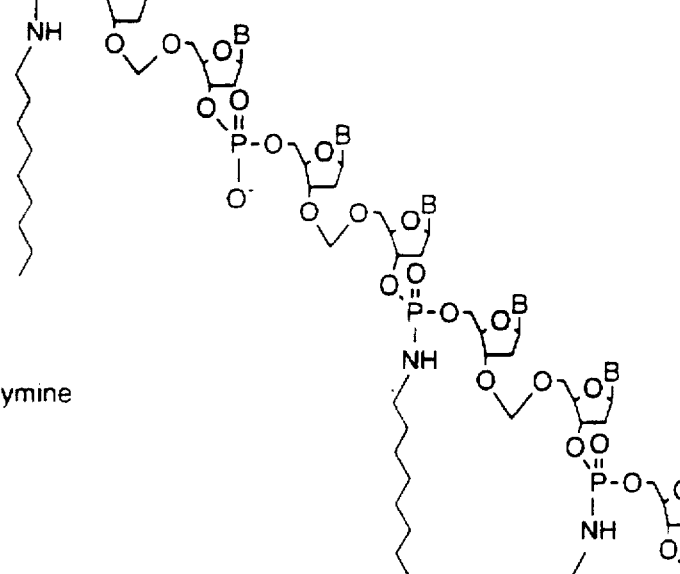

The structures of the listed compounds are given in FIG. 2. All of the listed compounds were soluble in aqueous solution to the extent that they could be visualized by fluorescence microscopy. Each compound entered cellular cytoplasm rapidly after addition to cells in tissue culture. As indicated in FIG. 2, the molecular weight of the compounds ranged from 846 daltons to 3484 daltons and, in the case of compound 273-22D, carried a negative charge. These results are the first examples known by the present inventors of efficient passive diffusion by oligonucleotide analogs into cells.

EXAMPLE 5

Synthesis of Monomers

The following compounds of the formula

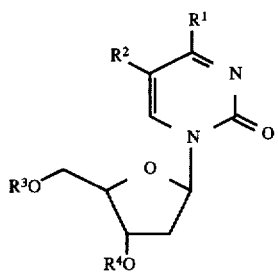

are shown in Table 1 and synthesized as described below.

TABLE I

| Cmp | R$^1$ | R$^2$ | R$^3$ | R$^4$ |
|---|---|---|---|---|
| 1 | OH | —C≡C—CH$_2$CH$_2$CH3 | H | H |
| 2 | OH | —C≡C—CH$_2$CH$_2$CH$_3$ | DMT | H |
| 3 | OH | —C≡C—CH$_2$CH$_2$CH$_3$ | DMT | HPO$_2^-$HTEA$^+$ |
| 4 | OH | —CH$_2$CH$_2$CH$_2$CH$_2$CH$_3$ | H | H |
| 5 | OH | —CH$_2$CH$_2$CH$_2$CH$_2$CH$_3$ | DMT | H |
| 6 | OH | —CH$_2$CH$_2$CH$_2$CH$_2$CH$_3$ | DMT | HPO$_2^-$HTEA$^+$ |
| 7 | OH | —CH$_2$CH$_2$CH$_2$CH$_2$CH$_3$ | DMT | —CH$_2$SCH$_3$ |
| 8 | OH | —CH$_2$CH$_2$CH$_2$CH$_2$CH$_3$ | H | TBS |
| 9 | OCH$_2$CH$_2$CH$_2$CH$_3$ | —CH$_3$ | DMT | H |
| 10 | OCH$_2$CH$_2$CH$_2$CH$_3$ | —CH$_3$ | DMT | HPO$_2^-$HTEA$^+$ |

DMT = 4,4'-dimethoxytrityl
TBS = t-butyldimethylsilyl
HTEA$^+$ = hydrogentriethylammonium 5-(1-Pentynyl)-2'-deoxyuridine (1).

This compound was prepared by the same procedure that Hobbs, F. W. J., *J Org Chem* (1989) 54:3420–3422, used for the preparation of other alkynyl substituted nucleosides. A mixture of 30.0 g (84.7 mmol) of 5-iodo-2'deoxyuridine (purchased from Sigma), 23.6 mL of 1-pentyne (Aldrich), 9.79 g of tetrakis (triphenylphosphine) palladium (0) (Aldrich), and 3.23 g of copper (I) iodide were stirred at room temperature for 26 h. To the reaction was added 250 mL of MeOH and 250 mL of CH$_2$Cl$_2$. The mixture was neutralized with Dowex 1×8-200 (bicarbonate form) ion exchange resin. The mixture was filtered and concentrated. The residue was partitioned between H$_2$O and CH$_2$Cl$_2$. The aqueous layer was extracted three times with CH$_2$Cl$_2$ and then concentrated. Purification of the crude product by column chromatography afforded 20.4 g (81.9% yield) of product.

5'-O-(4,4'-Dimethoxytrityl)-5-(1-pentynyl)-2'-deoxyuridine (2).

To 20.4 g (69.3 mmol) of 5-(1-pentynyl)-2'-deoxyuridine in 300 mL of dry pyridine was added 22.8 g of 4,4'-dimethoxytrityl chloride. The reaction was stirred for 17 h at room temperature and then concentrated. The residue was taken up in CH$_2$Cl$_2$ and washed twice with 0.5% aqueous NaHCO$_3$, dried (Na$_2$SO$_4$), filtered, and concentrated. Purification of the crude product by column chromatography afforded 21.9 g (52.9% yield) of product.

5'-O-(4,4'-Dimethoxytrityl)-5-(1-pentynyl)-2'-deoxyuridin-3'-O-yl-hydrogenphosphonate hydrogentriethylammonium salt (3).

To an ice-cold solution of 1.36 g (2.28 mmol) of 5'-O-(4,4'-dimethoxytrityl)-5-(1-pentynyl)-2'-deoxyuridine in 7.39 mL of dry pyridine and 17.8 mL of dry CH$_2$Cl$_2$ was added 9.30 mL of a 1.00M solution of 2-chloro-4H-1,3,2-benzodioxaphosphorin-4-one (purchased from Aldrich as a solid) in CH$_2$Cl$_2$, dropwise over two minutes. The reaction was stirred at 0° C. for 45 minutes and then poured onto a rapidly-stirred, ice-cooled mixture of 62 mL of 1M aqueous triethylammonium bicarbonate (TEAB, pH=8.2) and 31 mL of CH$_2$Cl$_2$. The mixture was stirred for 15 minutes and the layers were separated. The organic layer was washed with 1M aqueous TEAB, dried (Na$_2$SO$_4$), filtered, and concentrated. After isolation of the product by column chromatography on silica gel, the product was taken up in CH$_2$Cl$_2$, washed with 1M aqueous TEAB, dried (Na$_2$SO$_4$), filtered, and concentrated. This procedure afforded 938 mg (53.9% yield) of product.

5-Pentyl-2'-deoxyuridine (4).

To a solution of 1.03 g (3.50 mmol) of 5-(1-pentynyl)-2'-deoxyuridine in 25 mL of MeOH was added a catalytic amount of 10% Pd on charcoal. The mixture was hydrogenated under 300 psi of H$_2$ for 14 h at room temperature. The mixture was filtered through Celite and concentrated, affording a quantitative yield of product.

5'-O-(4,4'-Dimethoxytrityl)-5-pentyl-2'-deoxyuridine (5).

This compound was prepared from 1.04 g (3.49 mmol) of 5-pentyl-2'-deoxyuridine by the same procedure used for the preparation of 5'-O-(4,4'-dimethoxytrityl)-5-(1-pentynyl)-2'-deoxyuridine. Column chromatography of the crude residue on silica gel afforded 1.70 g (81.0% yield) of product.

5'-O-(4,4'-Dimethoxytrityl)-5-pentyl-2'-deoxyuridin-3'-O-yl-hydrogenphosphonate hydrogentriethylammonium salt (6).

This compound was prepared from 1.48 g (2.46 mmol) of 5'-O-(4,4'-dimethoxytrityl)-5-pentyl-2'-deoxyuridine by the same procedure used for the preparation of 5'-O-(4,4'-dimethoxytrityl)-5-(1-pentynyl)-2'-deoxyuridine-3'-yl-hydrogenphosphonate hydrogentriethylammonium salt. This procedure afforded 1.35 g (71.8% yield) of product.

5'-O-(4,4'-Dimethoxytrityl)-3'-O-methylthiomethyl-5-pentyl-2'-deoxyuridine (7).

To a solution of 3.50 g (5.83 mmol) of 5'-O-(4,4'-dimethoxytrityl)-5-pentyl-2'-deoxyuridine in 148 mL of dry THF was carefully (hydrogen evolution!) added 835 mg of sodium hydride (97%) in small portions at room temperature. After stirring the mixture for 30 minutes, 959 mg of sodium iodide (NaI) was added, followed by 0.557 mL of chloromethyl methyl sulfide (Aldrich). The reaction was stirred for 4 h and then carefully quenched with MeOH. The mixture was concentrated. The residue was partitioned between CH$_2$Cl$_2$ and H$_2$O, shaken, and separated.The organic layer was washed with sat. aqueous NaHCO$_3$, H$_2$O, dried (Na₂SO₄), filtered, and concentrated. The crude residue was purified by column chromatography on silica gel affording 2.76 g (71.7% yield) of product.
3'-O-t-Butyldimethylsilyl-5-pentyl-2'-deoxyuridine (8).

To a mixture of 3.50 g (5.83 mmol) of 5'-O-(4, 4'dimethoxytrityl)-5-pentyl-2'-deoxyuridine and 1.91 g of imidazole in 23.3 mL of dry DMF was added 1.05 g of t-butyldimethylsilyl chloride (purchased from Petrarch). The reaction was stirred at room temperature for 20 h and then concentrated. The residue was partitioned between CH₂Cl₂ and H₂O, shaken, and separated. The organic layer was washed with H₂O, and concentrated. The crude material was stirred in 150 mL of 80% HOAc in H₂O for 3 h and then concentrated. The residue was taken up in CH₂Cl₂ washed with H₂O, sat. aqueous NaHCO₃, dried (Na₂SO₄), filtered, and concentrated. Column chromatography of the crude residue afforded 1.88 g (78.3% yield) of product.
4-O-Butyl-5'-O-(4,4'-dimethoxytrityl)-thymidine (9).

To an ice-cold solution of 5'-O-(4,4'-dimethoxytrityl)-thymidine (2.0 g; 3.67 mmole) in 20 mL of CH₂Cl₂ was added 6 mL of N,N-dimethylaminotrimethylsilane. After stirring 30 min. at 0° C., the reaction mixture was concentrated to dryness. The crude residue was dissolved in 50 mL of acetonitrile. To this was added triethylamine (11 g; 110 mmoles) and 1,2,4-triazole (1.52 g; 22 mmoles), and the mixture cooled to 0° C. To this ice-cold mixture was added POCl₃ (1.10 g; 7.3 mmole). The reaction mixture was stirred at 0° C. for 3 h, then at room temperature overnight. The reaction was then concentrated. The residue was dissolved in CH₂Cl₂, and washed twice with saturated aqueous NaHCO₃. The organic phase was dried over Na₂SO₄, filtered, and concentrated. The residue was purified by column chromatography on silica gel, affording 2.20 g of triazole intermediate. The triazole intermediate (2.1 g; 3.5 mmole) was dissolved in anhydrous n-butanol (12 mL) and treated with DBU (1.0 g; 7.0 mmole). After one h, the reaction mixture was concentrated to dryness. The residue was dissolved in CH₂Cl₂, washed with 10% aqueous citric acid, dried over Na₂SO₄, and filtered. The residue was purified by column chromatography on silica gel, affording 1.0 g of product.

4-O-Butyl-5'-O-(4,4'-dimethoxytrityl)-thymidin-3'-O-yl-hydrogenphosphonate hydrogentriethylammonium salt (10).

This compound was prepared from 4-O-butyl-5'-O-(4,4'-dimethoxytrityl)-thymidine in the same manner as described for the preparation of 5'-O-(4,4'-dimethoxytrityl)-5-(1-pentynyl)-2'-deoxyuridin-3'-O-yl-hydrogenphosphonate hydrogentriethylammonium salt.

EXAMPLE 6

Synthesis of Dimer Synthons Containing Formacetal Linkages

The following dimers of the formula

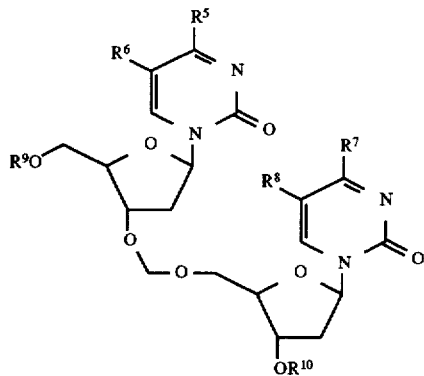

are shown in Table 2 and synthesized as described below.

5'-O-([5'-O-(4,4'-Dimethoxytrityl)-5-pentyl-2'-deoxyuridin-3'-O-yl]-methyl-5-pentyl-2'-deoxyuridine (11).

This compound was prepared from compounds 7 and 8 in the same manner as that previously described for the preparation of 5'-O-([5'-O-(4,4'-dimethoxytrityl)-thymidin-3'-O-yl]-methyl)-thymidine in U.S. Ser. No. 690,786 in 86% yield.

5'-O-([5'-O-(4,4'-Dimethoxytrityl)-5-pentyl-2'-deoxyuridin-3'-O-yl]-methyl)-5-pentyl-2'-deoxyuridin-3'-O-yl-hydrogenphosphonate hydrogentriethylammonium salt (12).

This compound was prepared from 5'-O-([5'-O-(4,4'-dimethoxytrityl)-5-pentyl-2'-deoxyuridin-3'-O-yl]-methyl-5-pentyl-2'-deoxyuridine using the same procedure described for the preparation of 5'-O-(4,4'-dimethoxytrityl)-5-(1-pentynyl)-2'-deoxyuridin-3'-O-yl-hydrogenphosphonate hydrogentriethylammonium salt.

5'-O-([5'-O-(4,4'-Dimethoxytrityl)-thymidin-3'-O-yl]-methyl)-thymidine (13).

This compound was prepared as described in U.S. Ser. No. 690,786.

TABLE 2

| Cmp | R⁵ | R⁶ | R⁷ | R⁸ | R⁹ | R¹⁰ |
|---|---|---|---|---|---|---|
| 11 | OH | —CH₂CH₂CH₂CH₂CH₃ | OH | —CH₂CH₂CH₂CH₂CH₃ | DMT | H |
| 12 | OH | —CH₂CH₂CH₂CH₂CH₃ | OH | —CH₂CH₂CH₂CH₂CH₃ | DMT | HPO₂⁻HTEA⁺ |
| 13 | OH | —CH₃ | OH | CH₃ | DMT | H |
| 14 | OCH₂CH₂CH₂CH₃ | —CH₃ | OCH₂CH₂CH₂CH₃ | CH₃ | DMT | H |
| 15 | OCH₂CH₂CH₂CH₃ | —CH₃ | OCH₂CH₂CH₂CH₃ | CH₃ | DMT | HPO₂⁻HTEA⁺ |

For abbreviations, see Table 1

5'-O-([4-O-Butyl-5'-O-(4,4'-dimethoxytrityl)-thymidin-3'-O-yl]-methyl)-4-O-butylthymidine (14).

This compound was prepared from 5'-O-([5'-O-(4,4'-dimethoxytrityl)-thymidin-3'-O-yl]-methyl)-thymidine by the same procedure used for the preparation of 4-O-butyl-5'-O-(4,4'-dimethoxytrityl)-thymidine. Column chromatography afforded a 52% yield of product.

5'-O-([4-O-Butyl-5'-O-(4,4'-dimethoxytrityl)-thymidin-3'-O-yl]-methyl)-4-O-butylthymidin-3'-O-yl-hydrogenphosphonate hydrogentriethylammonium salt (15).

This compound was prepared from 5'-O-([4-O-butyl-5'-O-(4,4'-dimethoxytrityl)-thymidin-3'-O-yl]-methyl-4-O-butylthymidine by the same procedure used for the preparation of 5'-O-(4,4'-dimethoxytrityl)-5-(1-pentynyl-2'-deoxyurdin-3'-O-yl-hydrogenphosphonate hydrogentriethylammonium salt.

EXAMPLE 7

Synthesis of Oligonucleotides

General Procedures

The pivaloyl chloride (trimethylacetylchloride) was purified by distillation at atmospheric pressure and stored under argon. The solvents (pyridine, dichloromethane, acetonitrile) were dried over activated molecular sieves (3 Å). The solvents used in the coupling cycle should be as anhydrous as possible to avoid any undesirable hydrolysis reactions. The starting dimethoxytrityl protected deoxynucleoside H-phosphonates were dried by co-evaporation from anhydrous acetonitrile and subsequently reconstituted in 1:1 anhydrous pyridine and acetonitrile. Synthesis was performed with the aid of a Biosearch Model 8700 DNA synthesizer employing solid support, preferably CPG (controlled pore glass).

Functionalization of Solid Support

To a solution of an appropriate nucleoside (such as 5'-O-(4,4'-dimethoxytrityl)-5-(1-pentynyl)-2'-deoxyuridine, 5'-O-(4,4'-dimethoxytrityl)-5-pentyl-2'-deoxyuridine, 4-O-butyl-5'-O-(4,4'-dimethoxytrityl)-thymidine, 5'-O-([5'-O-(4,4'-dimethoxytrityl)-5-pentyl-2'-deoxyuridin-3'-O-yl]-methyl)-5-pentyl-2'-deoxyuridine, 5'-O-([4-O-Butyl-5'-O-(4,4'-dimethoxytrityl)-thymidin-3'-O-yl]-methyl)-4-O-butylthymidine, or 5'-O-([5'-O-(4,4'-dimethoxytrityl)-thymidin-3'-O-yl]-methyl)-thymidine) in 12 mL of anhydrous pyridine containing triethylamine (TEA, 80 µl) was added 384 mg of DEC [1-(3-dimethylaminopropyl)-3-ethyl carbodiimide hydrochloride], 12 mg of DMAP (N,N-dimethylaminopyridine), and 1 g of CPG LCAA succinic acid (LCAA, long chain alkyl amine). The resulting mixture was sealed under argon, wrapped in foil, and shaken for 14 h. The amount of nucleoside loading was determined by the dimethoxytrityl cation assay described below.

Dimethoxytrityl Cation Assay for the Determination of Nucleoside Loading on Solid Support To 1 mg of functionalized CPG was added 1 mL of 0.1M p-toluenesulfonic acid monohydrate (TSA) in dichloromethane. The UV absorption of the solution using a standard cell was then measured at 498 nm. The degree of substitution (loading) was calculated using the following formula: substitution (µmole/g)=A498×14.3, where A=absorbance.

Nucleoside substitutions (loadings) achieved were typically between 20 and 40 µmole of nucleoside per gram of functionalized support. The unreacted succinic acid sites on the solid support were capped by adding 134 mg of pentachlorophenol and shaking the mixture for 16 h. This formed the corresponding ester. The mixture was filtered and the support was sequentially washed with pyridine, dichloromethane, and then diethylether. The support was then shaken with 10 mL of anhydrous piperidine in a 25 mL round bottomed flask for 5 min. The mixture was filtered and the support washed with dichloromethane and then diethylether. The support was then added to an anhydrous solution containing 2.5 mL of acetic anhydride, 10.0 mL of pyridine, and 10 mg of DMAP. The solution was placed under argon, capped, and shaken for 4 h. The mixture was filtered, and the functionalized CPG was washed sequentially with pyridine, dichloromethane, methanol and diethylether. The CPG was dried in vacuum and was then ready for solid phase oligonucleotide synthesis.

Preparation of DNA H-phosphonate

The oligonucleotide H-phosphonate having the following structures were prepared according to the following procedure. First, the functionalized (A for sequence A, B for sequence B) solid support was placed in a reactor vessel (column) and was washed with dichloromethane. Then, a 2.5% solution of dichloroacetic acid (DCA) in dichloromethane was introduced to remove the 5' protecting group of the support-bound nucleoside. After the deprotection step, the solid support was washed with dichloromethane, and then anhydrous pyridine/acetonitrile (1/1, by volume).

The first coupling cycle was initiated by the addition of a 1.5% solution of pivaloyl chloride in anhydrous pyridine/acetonitrile, 1/1) and ten equivalents (based on the amount of loading of the support bound nucleotide) of the appropriate protected nucleoside hydrogenphosphonate in anhydrous pyridine/acetonitrile (1/1) in alternating pulses. The reagents were allowed to react for 3.5 min.

At this point the oligonucleotide could be further extended by repeating the sequence of DCA deprotection and pivaloyl chloride coupling until the desired length and sequence of bases was attained. Alternatively, the linkage or linkages could be oxidized to the thiophosphate, phosphodiester or the phosphoramidate.

The final coupling for fluorescent labelling utilizes coupling of 6-N-(4-methoxytrityl)-aminohexan-1-O-yl)-hydrogenphosphonate hydrogentriethylammonium salt. The coupling of this hydrogenphosphonate was identical to the other hydrogenphosphonate couplings. After coupling and desired oxidation, the monomethoxytrityl protecting group was removed from the amine in a similar fashion as described above.

Conjugation of 5'Amino Linker Oligonucleotide with a Fluorescein Label

A 10 µmole reaction (calculated from the loading of the CPG in µm/g and the mass of the support bound nucleoside) was placed in 3.6 mL of anhydrous N,N-dimethylforamide (DMF) and 0.4 mL of disopropylethylamine. To this solution was added 24 mg of 5- (and 6-) carboxyfluorescein, succinimidyl ester. The reaction was capped and shaken in the dark for 10 h, and then filtered. The solid support was then sequentially washed with dichloromethane, DMF, water, methanol and then diethylether. The support-bound, fluorescently-labelled oligonucleotide was then washed to remove unconjugated carboxyfluorescein.

Oxidation of the Oligonucleotide H-Phosphonate to the Thiophosphate

The DNA H-phosphonate, prepared above, was converted directly to the thiophosphate, preferably while the DNA was still bound to the solid support, by the addition to the reactor vessel of 1 mL of an oxidizing mixture comprised of a 2.5% solution (by weight) of elemental sulfur (sublimed sulfur powder available from Aldrich Chemical Company, Milwaukee, Wis., USA, Cat No. 21,523-6) in anhydrous pyridine/carbon disulfide (1/1, v/v). The contents of the reactor were mixed for 20 min., and then the reagents were removed. This oxidation cycle was carried out a second time using 1 mL of an oxidizing solution comprising equal volumes of a 2.5 wt % solution of elemental sulfur in anhydrous pyridine/carbon disulfide (1/1, v/v) and 10% by volume diisopropylethylamine in anhydrous pyridine. Finally, the oxidized copolymer-bound oligonucleotide was washed with anhydrous pyridine/acetonitrile (1/1, v/v), followed by anhydrous dichloromethane.

Oxidation of the Oligonucleotide H-Phosphonate to the Phosphodiester and the Phosphoramidate Analog The oligonucleotide H-phosphonate was oxidized, when desired, to the phosphodiester derivative by the following procedure:

Method A

To the solid support, obtained from the process outlined above, was added 1 mL of an oxidizing solvent mixture comprised of 0.1M $I_2$ in water/pyridine (2/98, v/v). The resulting mixture was agitated for 15 min., and then the reagents were removed. Afterwards, 1 mL of a second oxidizing solvent mixture made from equal volumes of 0.1M $I_2$ in water/pyridine (2/98, v/v) and 0.1M triethyl ammonium bicarbonate in water/pyridine (1/9, v/v) was added to the solid support. After mixing the contents of the reactor for 5 min., the reagents were removed. Finally, the oxidized copolymer-bound product was washed with anhydrous pyridine/acetonitrile (1/1, v/v) and then anhydrous dichloromethane.

Method B

Alternatively, the oligonucleotide H-phosphonate was oxidized to the phosphoramidate analog by the following procedure: To the solid support, obtained from the procedure outlined above, was added 18 mL of an oxidizing solvent mixture made from 10% by volume of the desired amine in anhydrous/pyridine/carbon tetrachloride (1/1, v/v). The resulting mixture was agitated for 15 min., after which time the spent oxidizing solvent mixture was discarded. Finally, the oxidized copolymer-bound product was washed with anhydrous pyridine/acetonitrile (1/1, by volume), and then anhydrous dichloromethane.

The oligonucleotide H-phosphonates could be oxidized or converted to a number of other linkage derivatives, such as phosphoric acid triesters, dithiophosphoric acids, their corresponding esters and amidates, and other which are desirable to and which are within the skill of those knowledgeable in the art. Related oxidation procedures are described, for example, in application no. EP 0 219 342 by B. C. Froehler, the complete disclosure of which is incorporated herein by reference. Thus, oligonucleotides having a variety of linkages derived from phosphoric acid, such as phosphoric acid diesters, phosphoric acid triesters, thiophosphoric acid, dithiophosphoric acid, phosphoric acid thioesters, phosphoric acid dithioesters, phosphoric acid amidates, or thiophosphoric acid amidates, can be readily obtained from the methods described above.

Cleavage of the Oligonucleotide From the Copolymer Support

Once the synthesis of the oligonucleotide was complete, the DNA was cleaved from the solid support, with the concurrent removal of any base protecting groups, by the addition of concentrated aqueous ammonium hydroxide and heating the resulting mixture at 45° C. for 24 h. The product oligonucleotide was washed from the solid support with methanol/water.

Purification was effected by reverse-phase HPLC, under the conditions described further below.

HPLC Purification of the Fluorescently Labeled oligonucleotide

A crude sample containing approximately 10 μmole of the fluorescently labeled oligonucleotide, prepared by the methods described above, and dissolved in a solvent mixture of 1/1 (v/v) methanol/water (10 mL) was concentrated under vacuum. The oligonucleotide was resuspended in 1 mL of methanol and then diluted with 100 mM aqueous triethylammonium acetate (TEAA, pH 7.0) and 5% (by volume) aqueous acetonitrile to a final volume of 10 mL. This dilute oligonucleotide solution was then loaded, at a flow rate of 2 mL/min, on a Septech A/E 160 cm×10 cm i.d., column packed with Hamilton PRP-1 (polystyrene stationary phase, 12–20 μm), which had been preconditioned with 60 mL of a buffer solution comprised of 5% by volume of acetonitrile in 100 mM TEAA (Buffer C, pH=7.0) at a flow rate of 3 mL/min. After the completion of the sample loading a 45 min. linear gradient to 100% of Buffer D (75% by volume acetonitrile in 100 mM TEAA, pH=7.0) was initiated. After 45 min., a linear gradient of 100% Buffer B in 15 min. (100% acetonitrile) was initiated. The product was eluted and collected. The collected fractions were then dried in vacuum, and the excess TEAA salt was removed by co-evaporation 3× with 1 mL 90% ethanol, 10% water. The counter ion (if present) was then exchanged by passing the oligonucleotide (in 0.5 mL) over a Poly-Prep, Bio-Rad column (packing AG 50 w×8 Na form) and eluting with 3 mL of water to yield a highly pure fluorescently labeled oligonucleotide.

We claim:

1. An oligonucleotide and pharmaceutically acceptable salts thereof wherein said oligonucleotide contains at least two nucleoside residues, has a log Poct value of about 0.0–2.5 and a solubility in water of at least about 0.001 μg/mL.

2. The oligonucleotide of claim 1 wherein the log Poct value is about 1.0–2.2.

3. The oligonucleotide of claim 1 wherein either at least 80% of the internucleotide linkages are non-ionic or at least 80% of the bases included in said nucleosides contain a lipophilic substitution; or wherein the percent non-ionic nucleotide linkage and the percent bases containing lipophilic substitutions sum to at least 80%.

4. The oligonucleotide of claim 1 wherein either at least 60% of the internucleotide linkages are non-ionic or wherein at least 60% of the bases included in said nucleosides contain a lipophilic substitution; or wherein the percent non-ionic nucleotide linkage and the percent bases containing lipophilic substitutions sum to at least 60%.

5. The oligonucleotide of claim 3 wherein said non-ionic internucleotide linkages are selected from the group consisting of formacetal, 3'-thioformacetal, riboacetal, phosphoramidate substituted with a substituent of 3°–20° C., phosphotriesters containing a substituent of 3°–20° C., and thiophosphotriesters containing a substituent of 3°–20° C.

6. The oligonucleotide of claim 3 wherein said lipophilic substitution is selected from the group consisting of saturated and unsaturated pseudohydrocarbyl groups of 1-12C.

7. The oligonucleotide of claim 3 wherein said lipophilic substitution is selected from the group consisting of 1-8C hydrocarbyl substituents at C-5 of pyrimidines, N2 or C8 of guanine, N4 of cytosine and C7 of 7-deazapurines.

8. The oligonucleotide of claim 6 wherein the pseudohydrocarbyl group is selected from the group consisting of methyl, ethyl, vinyl, ethynyl, propyl, isopropyl, propenyl, propynyl, isobutyl, butenyl, butynyl, phenethyl, pentyl, pentenyl, isopentyl, butyl, pentynyl, and benzyl.

27

9. The oligonucleotide of claim 1 wherein at least one nucleoside is selected from the group consisting of thymidine, 2'-deoxycytidine, 2'-deoxy-5-methylcytidine, $N^6$-methyl-8-oxo-2'-deoxyadenosine, 2'-deoxy-5-vinylcytidine, 2'-deoxy-5-ethynylcytidine, 2'-deoxy-5-vinyluridine, 2'-deoxy-5-propynylcytosine, 2'-deoxy-5-propynyluridine, 2'-deoxy-5'-ethynyluridine, 2'-deoxyadenosine, 2'-deoxyguanosine, and 2'-deoxy-N7-deazaxanthosine.

10. The oligonucleotide of claim 1 wherein at least one nucleotide is substituted at the 2' position.

11. The oligonucleotide of claim 10 wherein said 2' substitution is selected from the group consisting of fluoro, O-methyl, O-propyl, O-butyl, S-propyl, S-butyl, S-methyl, O-ethyl, S-ethyl, O-allyl, and S-allyl.

12. The oligonucleotide of claim 1 coupled to a label.

13. The oligonucleotide of claim 12 wherein said label is a fluorescent moiety.

14. The oligonucleotide of claim 1 which is further characterized by the ability to bind single or double-stranded nucleic acid in a sequence-specific manner.

15. The oligonucleotide of claim 1 which is a dimer, trimer or tetramer.

16. A method to visualize cells which method comprises contacting the cells to be visualized with the oligonucleotide of claim 12 under conditions wherein passive diffusion across the cell membrane can occur so as to internalize said oligonucleotide;

washing the cells to remove any oligonucleotide which has not passively diffused across the membrane and become internalized; and detecting the oligonucleotide which has been internalized in the cells so as to visualize the cells.

17. The method of claim 16 wherein said oligonucleotide has a log Poct value of 0:0 for octanol:water as measured by reverse-phase HPLC.

18. The method of claim 16 wherein the oligonucleotide has a solubility of at least about 0.001 μg/mL in water.

19. The method of claim 16 wherein the cells are viable.

20. The method of claim 16 wherein a subcellular compartment of the mammalian cell is stained.

21. The method of claim 20 wherein a subcellular compartment is endoplasmic reticulum, nuclear envelope, nuclei or mitochondria.

22. The method of claim 16 which is further characterized by the ability to bind carbohydrate or nucleic acid or protein or lipid in a sequence-specific manner.

23. A method to permeate cells passively with an oligonucleotide which method comprises contacting said cells to be permeated with the oligomer of claim 1.

24. A method to assay a subcellular component which method comprises contacting the component to be assayed with the oligonucleotide of claim 12 under conditions wherein binding of the oligonucleotide to the component occurs;

separating unbound oligonucleotide from bound oligonucleotide; and detecting the bound oligonucleotide so as to assay the subcellular component.

28

25. The oligonucleotide of claim 1 of the formula

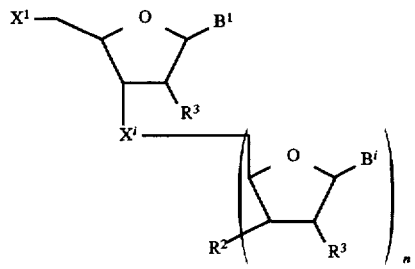

wherein $X^1$ is OH, OP($Z^1$)($Z^{1A}$)O or N(R)$_2$;

each $X^i$ is independently an internucleotide linkage selected from the group consisting of phosphodiester, phosphorothioate, phosphorodithioate, formacetal, 3'-thioformacetal, a phosphotriester having a pseudohydrocarbyl substituent (3-20C) and a phosphothiotriester having a pseudohydrocarbyl substituent (3-20C);

each $Z^1$ and $Z^{1A}$ is independently OH, $C_{1-10}$ O-alkyl or NHR;

R is H or $C_{1-6}$ alkyl;

$R^2$ is OH, a protecting group, H-phosphonate, methylphosphonate, β-cyanoethylphosphoramidite or a solid support;

each $R^3$ is independently H, OH, F, O-methyl, O-ethyl, O-propyl, O-isopropyl, O-butyl, O-isobutyl, O-propenyl or O-allyl;

each $B^1$ and $B^i$ is independently a purine or pyrimidine base optionally substituted with a lipophilic group;

n is an integer having a value of 1 to 27;

wherein said oligonucleotide is modified such that:

at least 60% of the internucleotide linkages are not phosphodiester linkages; or at least 60% of $B^1$ and $B^i$ contain the lipophilic group; or the percent non-phosphodiester linkages and the percent bases containing the lipophilic group sums to at least 60%.

26. The oligonucleotide of claim 25 wherein the lipophilic group at each base is a $C_{1-8}$ hydrocarbyl group that is optionally substituted with a heteroatom selected from the group consisting of nitrogen, oxygen and sulfur, wherein the $C_{1-8}$ hydrocarbyl group is linked to a purine or pyrimidine base position selected from the group consisting of a C5 position of pyrimidines, the O4 position of thymine, the N6 position of adenine, the C8 position of adenine, the N2 position of guanine, the C8 position of guanine, the N4 position of cytosine and the C7 position of 7-deazapurines.

27. The oligonucleotide of claim 25 wherein at least 80% of $B^1$ and $B^i$ contain the lipophilic group.

28. The oligonucleotide of claim 27 wherein each $X^i$ is independently a linkage selected from the group consisting of phosphorothioate, phosphorodithioate, phosphodiester, formacetal and 3'-thioformacetal.

29. The oligonucleotide of claim 25 wherein the octanol:water partition coefficient log Poct value is about 1.0–2.2.

30. The oligonucleotide of claim 29 wherein the lipophilic group at each base is a $C_{1-8}$ hydrocarbyl group that is optionally substituted with a heteroatom selected from the group consisting of nitrogen, oxygen and sulfur, wherein the $C_{1-8}$ hydrocarbyl group is linked to a purine or pyrimidine base position selected from the group consisting of a C5 position of pyrimidines, the O4 position of thymine, the N6 position of adenine, the C8 position of adenine, the N2 position of guanine, the C8 position of guanine, the N4 position of cytosine and the C7 position of 7-deazapurines.

31. The oligonucleotide of claim 29 wherein at least 80%, of $B^1$ and $B^i$ contain the lipophilic group.

32. The oligonucleotide of claim 31 wherein each $X^i$ is independently a linkage selected from the group consisting of phosphorothioate, phosphorodithioate, phosphodiester, formacetal and 3'-thioformacetal.

33. The oligonucleotide of claim 32 wherein each $X^i$ is independently a linkage selected from the group consisting of phosphorothioate, and phosphodiester.

34. The oligonucleotide of claim 25 wherein n is an integer having a value of 3 to 27.

35. The oligonucleotide of claim 34 wherein n is an integer having a value of 4 to 8.

36. The oligonucleotide of claim 1 or a salt thereof wherein said oligonucleotide contains internucleotide linkages selected from the group consisting of phosphodiester, phosphorothioate, phosphorodithioate, formacetal and 3'-thioformacetal, riboacetal, phosphoroamidate having a pseudohydrocarbyl substituent (3-20C), a phosphotriester having a pseudohydrocarbyl substituent (3-20C) or a phosphothiotriester having a pseudohydrocarbyl substituent (3-20C), and further wherein said oligonucleotide is modified such that:

at least 60% of the internucleotide linkages are non-ionic internucleotide linkages selected from the group consisting of formacetal and 3'-thioformacetal, riboacetal, a phosphotriester having a pseudohydrocarbyl substituent (3-20C) or a phosphothiotriester having a pseudohydrocarbyl substituent (3-20C);

at least 60% of the bases included in said oligonucleotide contain a lipophilic substitution at the N6 or C8 of adenine, the N2 or C8 of guanine or the C7 of 7-deazapurines; or the percent non-ionic nucleotide linkage and the percent bases containing lipophilic substitutions sum to at least 60%.

37. The oligonucleotide of claim 36 wherein the pseudohydrocarbyl substituent contains a nitrogen, oxygen or sulfur atom.

38. The oligonucleotide of claim 36 wherein the log distribution coefficient is about 1.0–2.2.

39. The oligonucleotide of claim 36 wherein the log distribution coefficient is about 0.26–1.61.

40. The oligonucleotide of claim 1 wherein the log distribution coefficient is about 0.26–1.61.

* * * * *